(12) United States Patent
Booher, Sr.

(10) Patent No.: US 10,463,530 B2
(45) Date of Patent: Nov. 5, 2019

(54) CERVICAL STABILIZATION DEVICE

(71) Applicant: ViaTechMD LLC, Scottsdale, AZ (US)

(72) Inventor: Benjamin V. Booher, Sr., Scottsdale, AZ (US)

(73) Assignee: ViaTechMD LLC, Scottsdale, AZ (US)

(*) Notice: Subject to any disclaimer, the term of this patent is extended or adjusted under 35 U.S.C. 154(b) by 699 days.

(21) Appl. No.: 14/734,737

(22) Filed: Jun. 9, 2015

(65) Prior Publication Data

US 2015/0265456 A1 Sep. 24, 2015

Related U.S. Application Data

(63) Continuation-in-part of application No. 14/047,828, filed on Oct. 7, 2013, which is a continuation-in-part of application No. 12/537,700, filed on Aug. 7, 2009, now Pat. No. 8,550,088.

(60) Provisional application No. 61/089,428, filed on Aug. 15, 2008, provisional application No. 61/164,815, filed on Mar. 30, 2009.

(51) Int. Cl.
A61B 17/425 (2006.01)
A61F 5/455 (2006.01)
A61F 6/08 (2006.01)

(52) U.S. Cl.
CPC ...................... A61F 6/08 (2013.01)

(58) Field of Classification Search
CPC .......... A61F 5/44; A61F 5/4404; A61F 5/442; A61F 5/451; A61F 5/455; A61F 5/4553; A61B 2017/4225; A61B 2017/4216; A61B 17/42

USPC ........... 128/DIG. 25, 841; 604/327–328, 330
See application file for complete search history.

(56) References Cited

U.S. PATENT DOCUMENTS

| 436,861 | A | * | 9/1890 | Sherwood ........... A61B 17/4241 128/836 |
| 1,162,568 | A | | 11/1915 | Carey |
| 2,400,251 | A | * | 5/1946 | Nagel ................ A61B 17/4241 606/119 |
| 2,638,093 | A | | 5/1953 | Kulick |
| 2,836,177 | A | | 5/1958 | Sells |
| 3,646,929 | A | | 3/1972 | Bonnar |
| 3,734,100 | A | | 5/1973 | Walker |
| 3,741,216 | A | | 6/1973 | Yosowitz et al. |
| 4,128,100 | A | | 12/1978 | Wendorff |
| 4,311,543 | A | | 1/1982 | Strickman et al. |
| 4,322,463 | A | | 3/1982 | Goepp |
| 4,381,771 | A | | 5/1983 | Gabbay |
| 5,167,237 | A | | 12/1992 | Rabin et al. |

(Continued)

FOREIGN PATENT DOCUMENTS

| CA | 2926704 | 4/2015 |
| JP | 2001511022 | 8/2001 |

(Continued)

Primary Examiner — Kari K Rodriquez
Assistant Examiner — Camtu T Nguyen
(74) Attorney, Agent, or Firm — Booth Udall Fuller, PLC

(57) ABSTRACT

A system and method for stabilizing an incontinent cervix during pregnancy are described. A system may include a nesting portion designed to surround the cervix without applying pressure to the cervix, while supporting the uterus in opposition to the weight of the developing fetus to prevent untimely effacement and dilatation of the cervix, thereby reducing the risk of premature birth and its consequence.

16 Claims, 21 Drawing Sheets

(56) References Cited

U.S. PATENT DOCUMENTS

| | | | |
|---|---|---|---|
| 5,209,754 A | * | 5/1993 | Ahluwalia ......... A61B 17/0218 |
| | | | 600/207 |
| 5,222,485 A | | 6/1993 | Jerath |
| 5,603,685 A | * | 2/1997 | Tutrone, Jr. ............ A61F 2/005 |
| | | | 128/836 |
| 5,827,248 A | | 10/1998 | Crawford |
| 5,851,188 A | | 12/1998 | Bullard et al. |
| 6,113,580 A | | 9/2000 | Dolisi |
| 6,526,980 B1 | | 3/2003 | Tracy et al. |
| 6,592,560 B2 | | 7/2003 | Snyder |
| 6,923,185 B1 | | 8/2005 | Koch |
| 6,994,678 B2 | | 2/2006 | Baxter-Jones et al. |
| 7,153,280 B2 | | 12/2006 | Welch |
| 8,408,212 B2 | | 4/2013 | O'Brien et al. |
| 2005/0277948 A1 | | 12/2005 | Cedars et al. |
| 2007/0067041 A1 | | 3/2007 | Kotoske |
| 2007/0203429 A1 | | 8/2007 | Ziv |
| 2007/0225744 A1 | | 9/2007 | Nobles et al. |
| 2008/0154284 A1 | | 6/2008 | Varma |
| 2008/0171974 A1 | | 7/2008 | Lafontaine |
| 2008/0269773 A1 | | 10/2008 | George |
| 2012/0136199 A1 | | 5/2012 | Hou et al. |

FOREIGN PATENT DOCUMENTS

| | | |
|---|---|---|
| KR | 20010110556 | 12/2001 |
| RU | 103470 | 4/2011 |
| WO | WO8102389 | 9/1981 |
| WO | 2008/058545 | 5/2008 |
| WO | 2010114577 | 10/2010 |
| WO | 2015159291 | 10/2015 |

* cited by examiner

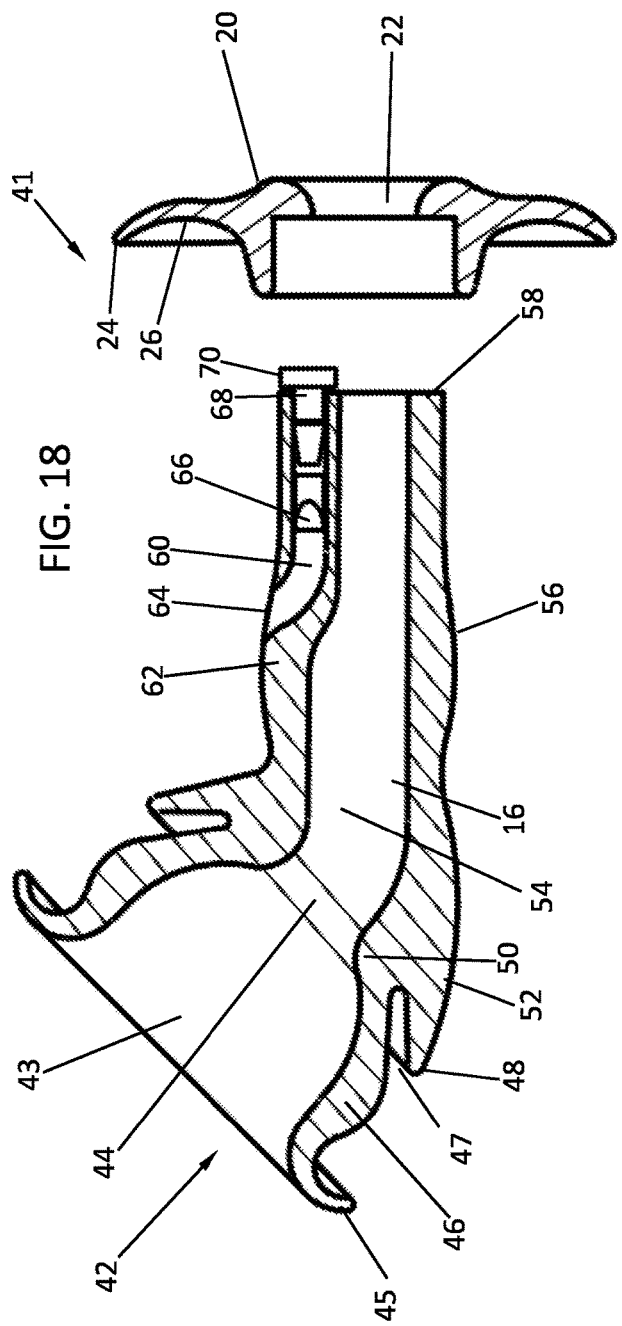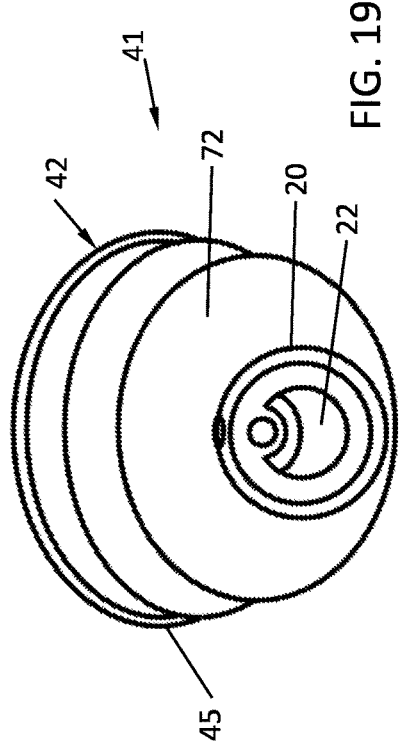

CERVICAL STABILIZATION DEVICE

CROSS REFERENCE TO RELATED APPLICATIONS

This application is a continuation-in-part of U.S. application Ser. No. 14/047,828 filed Oct. 7, 2013, entitled "Cervical Stabilization Device" to Benjamin V. Booher, Sr., now pending, which application is a continuation-in-part of U.S. application Ser. No. 12/537,700 filed Aug. 7, 2009, entitled "Cervical Stabilization Device" to Benjamin V. Booher, Sr., now U.S. Pat. No. 8,550,088 issued Oct. 8, 2013, which application claims priority to both U.S. Provisional Patent Application 61/089,428, filed Aug. 15, 2008, and to U.S. Provisional Patent Application 61/164,815, filed Mar. 30, 2009, the disclosures of each of which are hereby incorporated by reference in their entirety.

BACKGROUND

1. Technical Field

This disclosure relates to implementations of a device, with at least some portion thereof designed to be inserted into the vagina, for the purpose of stabilizing the cervix and uterus during pregnancy. Particular implementations may reduce the risk of miscarriage, premature delivery, premature rupture of membranes or stillbirth, resulting from bearing forces acting upon the cervix and/or compromise of the organs and structures of the female reproductive system.

2. Background Art

A medical condition commonly known as an "incontinent cervix" (also known as an "insufficient cervix", "incompetent cervix" and "loose cervix") can have serious effects on a pregnant woman and is known to be responsible for the loss of millions of preterm infants each year. Moreover, infants surviving preterm birth often suffer crippling lifelong diseases including autism and cerebral palsy (conditions known to result from premature birth). During a pregnancy, the fetus grows in the uterus, often referred to as the womb. As the fetus grows heavier, the weight bearing down upon the uterus strains upon the cervix. A patient with an incontinent cervix has a weakened cervix that may not be able to handle the added pressure on the cervix resulting from pregnancy. A common treatment for the incontinent cervix is to suture the cervix closed to prevent the cervix from opening further, in a procedure called a cerclage.

Such a condition, with or without cerclage, often requires that the patient be subject to bed rest for an extended period of time. Moreover, cerclage is known to further compromise the cervix which can make future pregnancies even more difficult, and the procedure is also often associated with an instantaneous premature birth event. Therefore, it is desirable to have a non-invasive, non-surgical method of treatment for incontinent cervix in order to retain the fetus in the womb until a viable birth is possible.

SUMMARY

Aspects of this disclosure relate to methods and structure for stabilizing a cervix during pregnancy. In one aspect, a device for stabilizing a cervix of a uterus during pregnancy may comprise a cervical cup configured to receive a cervix extending from a uterus that is carrying a fetus, the cervix comprising a cervical canal and an outer surface extending from a vaginal wall into a vagina. The cervical cup may comprise a cervical cup lip surrounding a void that is larger than an outer dimension of the cervix so that the cervical cup surrounds but does not intentionally engage the outer surface of the cervix between an entry of the cervix into the vagina and the opening of the cervical canal. The device may further comprise a core portion comprising a vent that is fluidly coupled to the cervical cup and at least one bladder portion coupled to the core portion and located at a position such that the at least one bladder portion does not contact the cervical cup when the at least one bladder portion is in an inflated state.

Particular implementations of a device for stabilizing a cervix may comprise one or more of the following: The cervical cup and core portion may be fluidly coupled by a flexural moment center configured to allow the cervical cup to flex relative to the core portion such that the cervical cup lip surrounds the cervix when the cervix is in a tipped position. The at least one bladder portion may further comprise an inflation valve configured to pass a fluid into the at least one bladder portion. The at least one bladder portion may comprise an inner balloon housed within an outer balloon. The at least one bladder portion may comprise at least one cleat on an outer surface of the at least one bladder portion configured to engage at least a portion of the vaginal wall. An outer surface of the at least one bladder portion may be comprised of a medical grade silicone having a hardness within a range of 20 to 60 durometer on the Shore A scale. The inner balloon may be comprised of a material having a gas permeability effect that is less than or equal to 30 in units of $10^8$ cm$^2$/(sec·atm). The inner balloon may be comprised of latex or polyurethane and the outer balloon is comprised of a medical grade silicone. The cervical cup may be comprised of a material having a hardness rating in a range of 40 to 80 durometer on the Shore A scale. The flexural moment center may further comprise a concave core portion contour.

In yet another aspect, a method of stabilizing a cervix during pregnancy may comprise at least partially surrounding a cervix of a uterus carrying a fetus with a cervical cup lip of a cervical cup of a cervical stabilization device without intentionally engaging an outer surface of the cervix between an entry of the cervix into the vagina and an opening of the cervical canal. The method may further comprise permitting the cervix to drain fluid from the cervical cup through a core portion of the cervical stabilization device that passes at least partially through a vagina and is in fluid communication with the cervical cup and at least partially inflating at least one bladder portion of the cervical stabilization device that is coupled to the core portion of the cervical stabilization device and is located at a position such that the at least one bladder portion does not contact the cervical cup when the at least one bladder portion is at least partially inflated.

Particular implementations of a method of stabilizing a cervix may comprise one or more of the following: The method may further comprise adjusting a position of the cervical cup to allow the cervical cup lip to surround a cervix that is in a tipped position by flexing a flexural moment center that couples the cervical cup to the core portion of the cervical stabilization device. The method may further comprise at least partially inflating the at least one bladder portion of the cervical stabilization device comprises passing a fluid through an inflation valve the at least one bladder portion further comprises an inflation valve configured to pass a fluid into the at least one bladder portion. The method may further comprise at least partially inflating the at least one bladder portion of the cervical stabilization devices comprises inflating an inner balloon that is housed within an outer balloon. The method may further comprise engaging at least one cleat-like contour on an outer surface of the at least one bladder portion of the cervical stabilization device with at least a portion of a vaginal wall when the at least one bladder portion is at least partially inflated. In some aspects, an outer surface of the at least one bladder portion of the cervical stabilization device may be comprised of a medical grade silicone having a hardness within a range of 20 to 60 durometer on the Shore A scale. In some aspect, the inner balloon of the cervical stabilization device that is at least partially inflated may be comprised of a material having a gas permeability effect that is less than or equal to 30 in units of 10^8 cm^2/(sec·atm). In some aspects, the inner balloon of the cervical stabilization device that is at least partially inflated may be comprised of latex or polyurethane and the outer balloon of the cervical stabilization device is comprised of a medical grade silicone. In some aspects, the cervical cup of the cervical stabilization device that at least partially surrounds the cervix may be comprised of a material having a hardness rating in a range of 40 to 80 durometer on the Shore A scale. In some aspects, the position of the surgical cup may be adjusted by changing an angle at which the cervical cup is positioned relative to the core portion of the cervical stabilization device by flexing a concave core portion contour of the flexural moment center.

The foregoing and other aspects, features, and advantages will be apparent to those having ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and:

FIG. 18 is an exploded cross section illustration of the second additional embodiment of a cervical stabilization device of FIG. 16 with the inflatable balloon removed;

FIG. 19 is an end view of a second additional embodiment of a cervical stabilization device;

DETAILED DESCRIPTION

Figure 1:
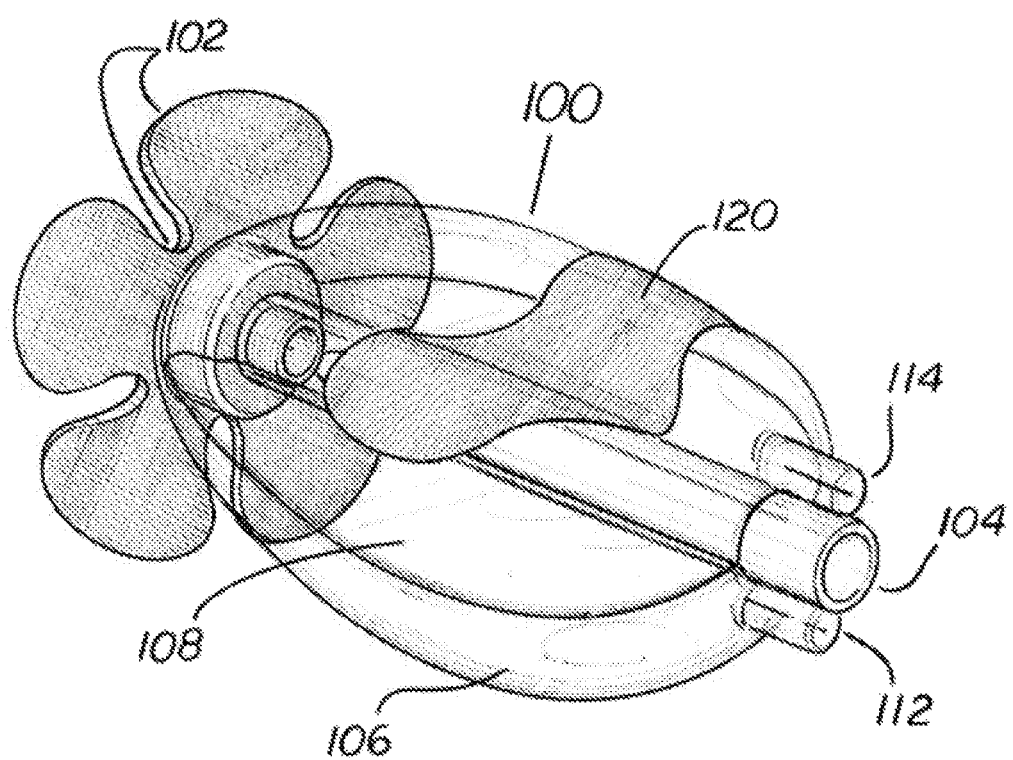
FIG. 1 is an isometric diagram illustrating one particular embodiment of a cervical stabilization device fully inflated, un-conformed, and outside the vagina confines.

The following descriptions are of exemplary embodiments of particular implementations of cervical stabilization devices and are not intended to limit the scope, applicability or configuration of the claims in any way. Rather, the following descriptions are intended to provide convenient illustrations for implementing various embodiments of cervical stabilization devices. As will become apparent, changes may be made in the function and/or arrangement of any of the elements described in the disclosed exemplary embodiments without departing from the spirit and scope of the claims.

Embodiments provide for a device that is used to stabilize the cervix, relieving some of the weight bearing down upon the cervix as the uterus ripens so as to reduce strain on or stimulation of the cervix. Conventional devices, used as contraceptives or to retain prolapsed organs (such as the bladder, bowel, and uterus) and which are not used or intended for use during pregnancy or to prevent premature births, and those used to clamp the cervix without supporting the uterus, force contact on the cervix by primitive engagement, clamping or pinching of the cervix. Particular implementations of a cervical stabilization device disclosed herein present light, incidental contact on the cervix, so as not to stimulate or damage the cervix. Specifically, implementations of cervical stabilization devices are not intended to engage the cervix to any functional degree until late stage effacement and dilation has progressed such that the amniotic sac is no longer sufficiently supported by the thinning/transforming cervix, at which time the present device then acts to provide support to the transformed cervical tissues to prevent premature rupture of membranes (known as PROM).

Implementations of the present device support the uterus, not the cervix, in order to resist the force upon the cervix that is known to accelerate effacement and dilation of the cervix which can lead to a premature birth and PROM.

One particular embodiment comprises a mechanical device, manufactured from a substance having at least a minimal degree of flexibility, such substance including, but not limited to, rubber, plastic, silicone polymer or other suitable material. The substance from which the device is manufactured may additionally comprise at least one embedded antibiotic accomplished by methods known in the art.

The device functions to provide a protective 'nest' to the cervix, surrounding at least a portion of the cervical tissue to prevent the pressure and weight of the developing fetus from extending the uterus deeper into the vagina, which can cause the cervix to efface and dilate. The nest serves to create a space for the cervix to reside, where it is not stimulated or in significant contact with the device. To stabilize the cervix without damaging tissue or compromising the natural "transformation" and biologies of the ectocervical tissues and mucous plug as the pregnancy advances, a particular implementation of the device comprises a uterine support shoulder configured to contact a portion of the vaginal wall proximate the entry of the cervix of the uterus into the vagina (an area known as the cervical fornices). The shoulder and nest are coupled to an annular portion surrounded by a bladder portion that first disposes bearing forces upon the resilient tissues of the vaginal wall, to terminate opposing the tissues proximate the lower pelvic structure (generally, the sacrum, pubis, ischium, and pubic symphysis). In contrast, conventional devices, used as contraceptives or to retain prolapsed organs (such as the bladder, bowel, and uterus) and which are not used or intended for use during pregnancy or to prevent premature births, and those used to clamp the cervix without supporting the uterus, force contact on the cervix by primitive clamping or pinching the more delicate and reactive tissues of the cervix. The present device can be produced in a wide range of geometries to assure the best fit and comfort of the patient. Alternately, ultrasound or other imagining technologies may be utilized to map the patient's exact physical proportions and a fully custom-fit device can be quickly manufactured by a laboratory or other suitable manufacturer. Still alternatively, molding techniques may be used by inserting a moldable substance into the patient's vagina to map certain of the patient's exact physical proportions and a custom-fit device can then be manufactured.

As the need arises, the device can be easily deflated, removed and replaced in a simple procedure that may additionally be non-surgical and anesthetic-free, allowing the attending physician's close inspection of the cervix and surrounding tissues as the pregnancy progresses. As delivery time approaches, the device can be deflated quickly and painlessly removed with little or no recovery time necessary, thereby allowing for the most natural delivery possible. Furthermore, as the patient's uterus expands, a cervical stabilization device of an accommodating size may be substituted for the previously used cervical stabilization device adapted to the growing fetus and resulting changes in uterus size and other physical factors to the patient's anatomy.

FIG. 1 illustrates a particular implementation of a cervical stabilization device. It should be understood that the embodiment in FIG. 1 is an embodiment illustrated outside of the human body and fully inflated. Cervical stabilization device 100 comprises a cervical nest 102 coupled to a vent tube 104. Vent tube 104 allows the natural discharges from the cervix to leave the body. Cervical nest 102 includes an enhanced contact portion surrounding a center, generally concave void portion, as seen more clearly in later illustrations. Surrounding vent tube 104 are inflatable bladder portions 106 and 108. Inflatable bladder portions 106 and 108 are inflated via inflation valves 112 and 114. Coupled to inflatable bladder portions 106 and 108 illustrated in FIG. 1, is an organ bridge 120. An organ bridge, or bridges, may be used to dispose of pressure that might otherwise compromise the function of surrounding organs such as the bladder and bowel.

Cervical nest 102 is designed to gently 'nest' the cervix while the uterine support shoulder portion (not shown in FIG. 1) bears the weight and force of the developing fetus forcing down upon the cervix, disposing such forces to the more resilient vaginal wall tissues, thereby reducing the forces acting on the cervix and the likelihood of preterm delivery.

Cervical nest 102 may be considered an optional component to the device 100, as the balloon portions may provide much of the same support. However, the cervical nest 102 allows for optimal cervical 'nesting' when carefully fitted to the patient by an appropriate healthcare professional, who may also be responsible for selecting the correct component sizes and the proper degree of inflation for each of the individual bladder portions.

Inflatable bladders portions 106 and 108 may be inflated by saline, air, inert gas, gels or any other suitable fluid(s) or materials, or otherwise inflated by decompressing a compressed material such as a foam, sponge or other bladder portion that has been compressed and can controllably be allowed to return toward its uncompressed state. The inflation may be precisely adjusted to provide a wide range of personal fit and adaptation to the patient's physical characteristics and needs. Inflation valves 112 and 114 may be designed to extend beyond the vaginal opening to maximize comfort, and allow the attending professional easy access for monitoring and adjusting the device. Alternatively, they may be terminated inside the vagina and accessed for adjustments as needed. In certain circumstances, termination inside the vagina may provide for a more comfortable device for mobile patients.

Inflatable bladder portions 106 and 108 may be made from a selection of suitable elastomeric materials, which may include but are not limited to rubber, plastic, or silicone-based materials capable of being formed into balloon portions and inflated or filled by any suitable methods to conform to a wide range of individual patient bio geometries. Alternatively, inflatable bladder portions 106 and 108 may be made from any suitable sponge-like or compressible material, including those materials that fall into the general range of 20 to 50 durometer on the Shore A Scale. It may be desirable for inflatable bladder portions 106 and 108 to be made from a transparent elastomer material, so that it is easier for the attending physician to remain visually apprised of the overall condition of the vaginal tissues. Furthermore, it may be desirable for the elastomer to be coated or embedded with antibiotics to protect from the risk of infection, and for the surface of inflatable bladder portions 106 and 108 to be textured to some extent to help secure its position within the vagina.

Figure 2:
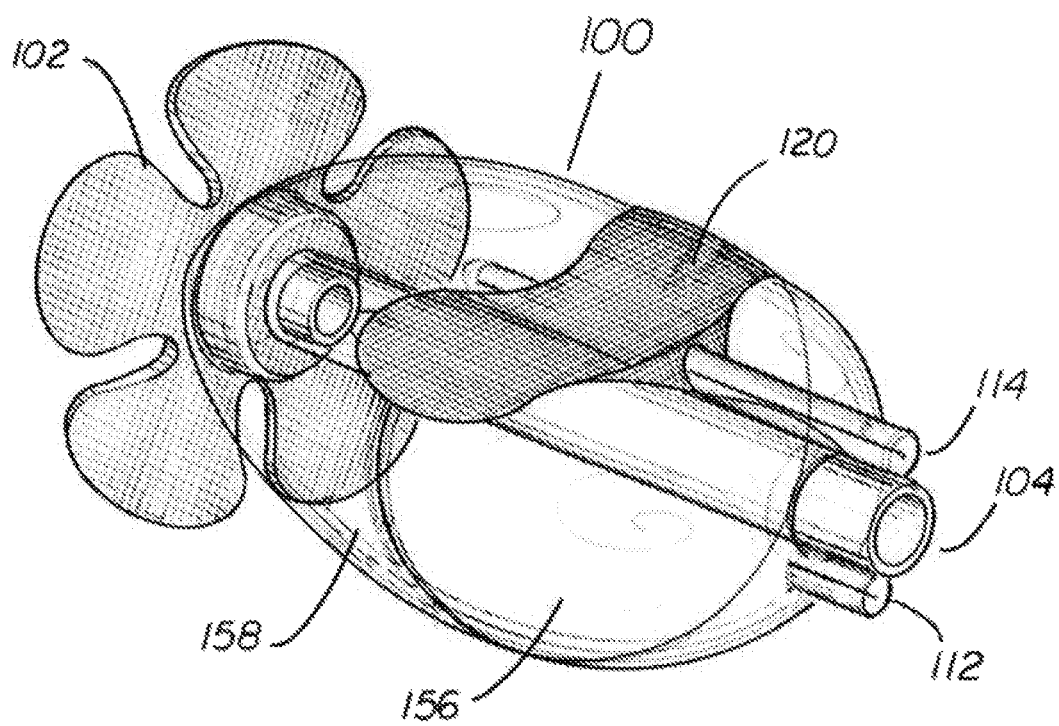
FIG. 2 is an isometric diagram illustrating another particular embodiment of a cervical stabilization device fully inflated, un-conformed, and outside the vagina confines.

FIG. 2 illustrates an alternative configuration of cervical stabilization device 100. Cervical nest 102, vent tube 104, inflation valves 112 and 114, and organ bridge 120 are as described above with respect to FIG. 1. The key difference between FIG. 1 and FIG. 2 are the inflatable bladder portions. In FIG. 1, inflatable bladder portions 106 and 108 are longitudinally opposed about vent tube 104. In FIG. 2, inflatable bladder portions 156 and 158 are annular vessels opposed about the axis of vent tube 104.

While both FIG. 1 and FIG. 2 show the use of two inflatable bladder portions, it should be understood that a single inflatable bladder may also be used. In addition, three or more inflatable bladder portions may also be used.

Figure 3:
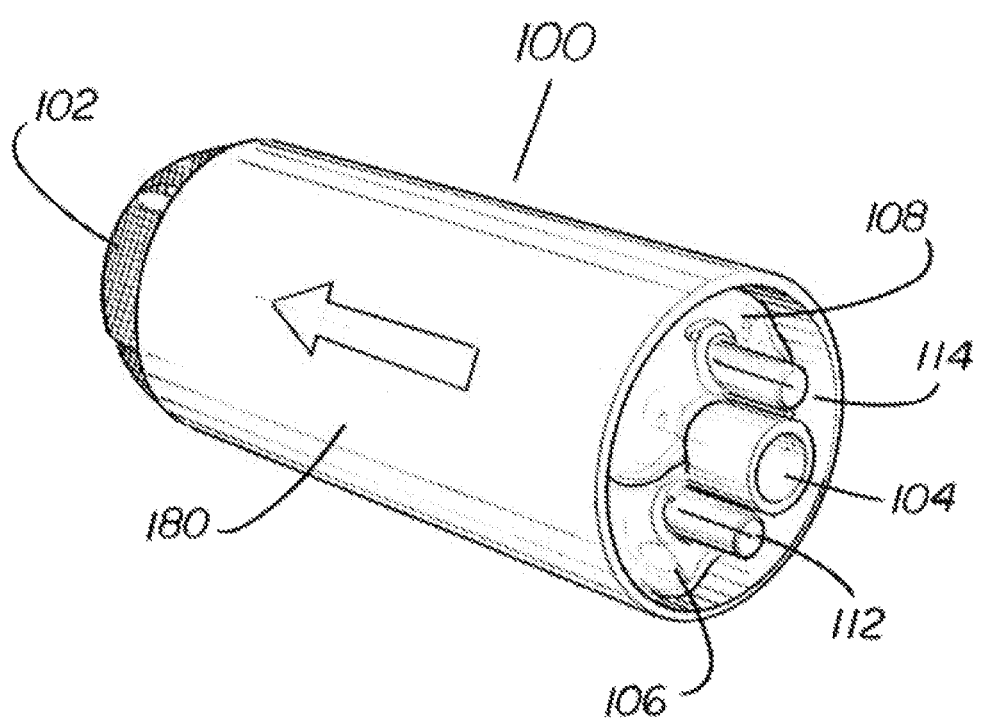
FIG. 3 illustrates a particular embodiment of a cervical stabilization device confined within an insertion sleeve.

FIG. 3 illustrates an embodiment of cervical stabilization device 100 in its deflated state. Cervical nest 102 has been folded and inflatable bladder portions 106 and 108 have been deflated such that cervical stabilization device 100 can be placed in insertion sleeve 180. Cervical stabilization device 100 is inserted into the patient in the direction of the arrow. Then the insertion sleeve 180 is removed and inflatable bladder portions 106 and 108 are inflated through the use of inflation valves 112 and 114.

Figure 6:
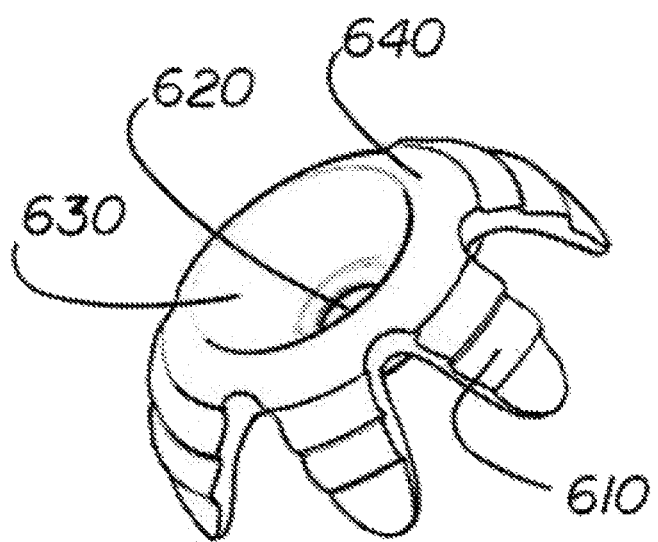
FIG. 6 is a detailed illustration of another particular embodiment of a cervical stabilization device.

FIG. 6 illustrates an isometric view of an embodiment that does not include inflatable bladder portions. The cervical stabilization device includes a seat portion 610, a vent 620, a central nesting area 630, and a uterine support shoulder 640. The central nesting area includes a generally concave void into which the cervix resides. The generally concave void is larger than the cervix, so that the nesting area surrounds and protects the cervix but does not purposefully engage, grip, squeeze, clamp or pinch the delicate and reactive cervical tissues as is common with conventional attempts to treat incontinent cervix. Vent 620 allows natural passage of discharges from the cervical canal to promote more normal biological function and to lessen the risk of infection or irritation of the cervix. Uterine support shoulder 640 occupies the space between the seat portion 610 and the nesting area 630. Uterine support shoulder 640 is coupled to and circumscribes nesting area 630. Seat portion 610 is depicted as having a plurality of portions extending from the uterine support shoulder 640. However, it should be understood that any number of seat portions, including a single circumferential seat portion, may be used in particular implementations. The operation of the seat portion 610, central nesting area 630, and uterine support shoulder 640 is similar to that described in the embodiment depicted in FIG. 4. Seat portion 610 is shown as having a plurality of ridges. However, it should be understood that seat portion 610 can also comprise a smooth surface, if it is desired to have less stress on the patient's vaginal walls.

Figure 7:
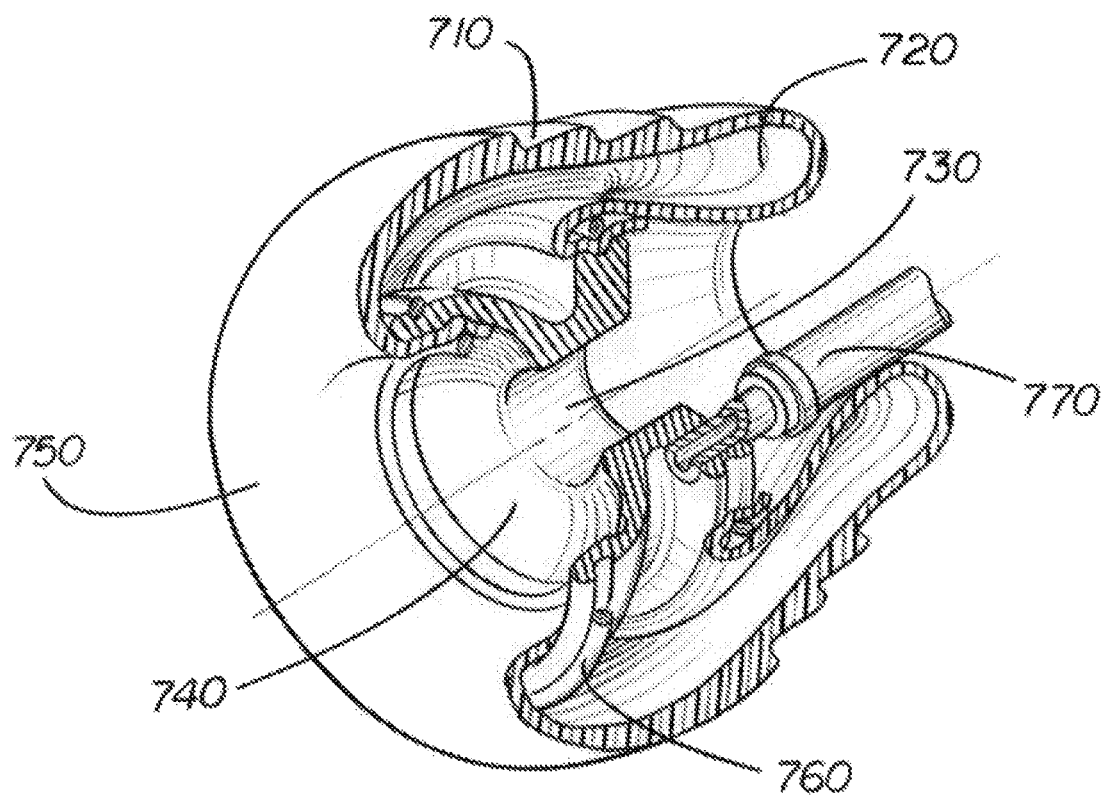
FIG. 7 is an isometric cross section illustration of another particular embodiment of a cervical stabilization device.

FIG. 7 illustrates an isometric cutaway view of another embodiment of the cervical stabilization device, including a cutaway view to show the interior of the design. The cervical stabilization device includes a seat portion 710, integral to inflatable bladder portion 720, a vent 730, a central nesting area 740, a uterine support shoulder 750, a radiologic placement ring 760 and an inflation valve assembly 770. The central nesting area 740 includes a generally concave void wherein the cervix resides and is protected. The generally concave void is larger than the cervix, so that the nesting area surrounds the cervix, but does not purposefully engage, grip, squeeze, clamp or pinch the delicate and reactive tissues of the cervix. Vent 730 allows natural passage of discharges from the cervical canal to promote more normal biological function and to lessen the risk of infection or irritation of the cervix. Uterine support shoulder 750 occupies the space between the seat portion 710 and the central nesting area 740. Bladder 720 may be inflated by saline, air, inert gas, gels or any other suitable fluid(s) or constructed to include flexible materials, or otherwise inflated by decompressing a compressed material such as a foam, sponge or other bladder portion that has been compressed and can controllably be allowed to return toward its uncompressed state. As bladder 720 is inflated, the interaction between the vaginal walls and seat portion 710 can be optimized to the patient's physical characteristics and needs. It should be understood that seat portion 710 can also be replaced by a smooth surface, if it is desired to place less stress on the patient's vaginal walls.

Figure 4:
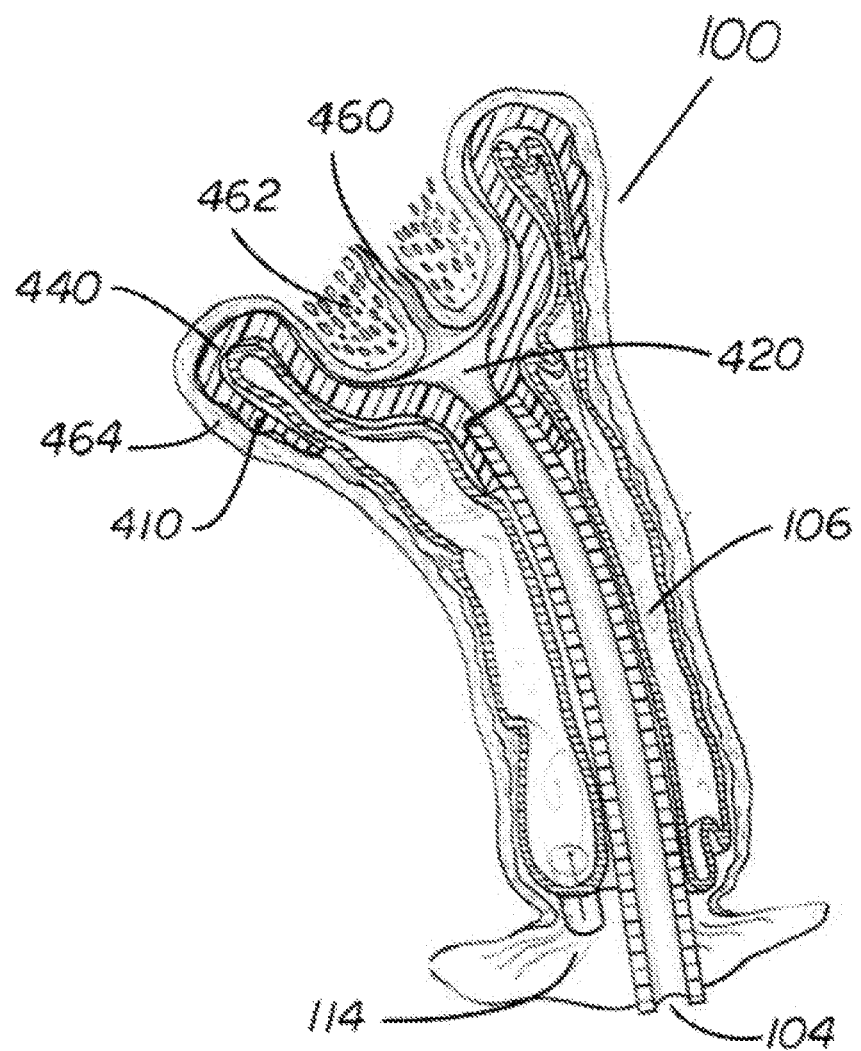
FIG. 4 is a cross section illustration of a particular embodiment of a cervical stabilization device positioned within the patient prior to inflation.

FIG. 4 is a cross sectional illustration of an embodiment of cervical stabilization device 100 that is fitted within a patient. A single inflatable bladder embodiment is shown, with inflatable bladder 106 surrounding vent tube 104. While shown in a deflated state, it should be understood that inflatable bladder 106 can be inflated through the use of inflation valve 114. The patient's anatomy as illustrated includes cervical canal 460, ectocervix 462, and vaginal wall 464.

In operation, as the ever increasing weight of the developing fetus produces forces upon the uterus which then involves the ectocervical tissue and may cause accelerated effacement and dilation of the compromised cervix leading to a premature birth or PROM, the cervical stabilization device 100 protects and stabilizes the cervix and ectocervix 462 by supporting the uterus via uterine support shoulder 440 and disposing the pressure to the more resilient vaginal wall 464, aided by the use of seat portions 410. Natural discharges from the cervix can travel through vent 420, which is coupled to vent tube 104.

Another particular implementation of the device comprises a structure providing support to the cervix without involving the vaginal wall. This implementation is particularly useful when a patient has sensitivities or conditions that might contraindicate involving the vaginal tissues (such as severe varicose veins or other medical conditions). One purpose for using this implementation includes providing the same gentle cradling of the cervix while limiting further settling and extension of the uterus into the vagina which is synchronous to the cervical effacement and dilation process.

Figure 5:
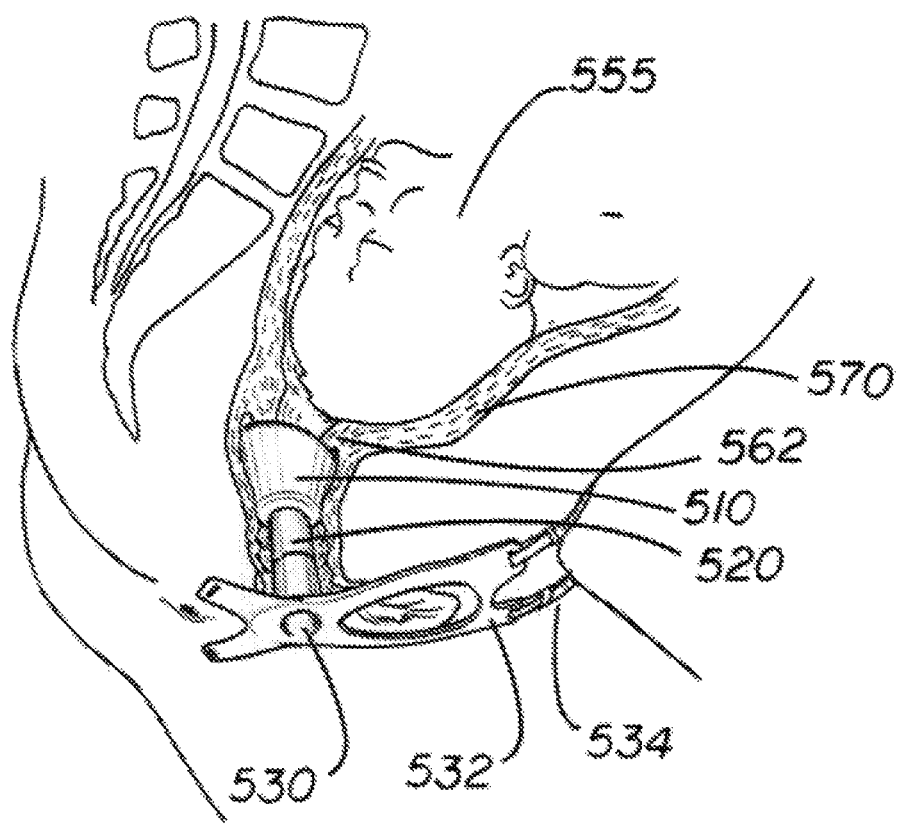
FIG. 5 is a cross section illustration of another particular embodiment of a cervical stabilization device inserted into a patient.

Referring now to FIG. 5, an adjustable nest 510 (including one or more accommodating features, as described above), is affixed to a support 520, which may be adjustable or selectable in length to accommodate various stages of pregnancy, and extends beyond the vaginal opening to a retaining portion 532 that is in turn supported by adjustable straps 534 which attach to a belt portion of the apparatus (not shown), or which may be held in position by other appropriate garment(s). Also illustrated is a vent 530, which serves the same purpose as the vents described above. Those portions in total provide a fully adjustable and reliable alternative to the more discreet, internal implementations previously described. Thus, the cervix 562 is supported to relieve pressure from developing fetus 555 within uterus 570. Individual components of a cervical stabilization device may be made from flexible polymers such as silicone-based rubber or gum, polyurethane or other suitable materials. More rigid components of a cervical stabilization device, such as the support 520, may be made of less flexible polymers or other suitable materials. The flexible form-fitting components are intended to fit comfortably and comply with individual patient bio geometries.

Figure 8:
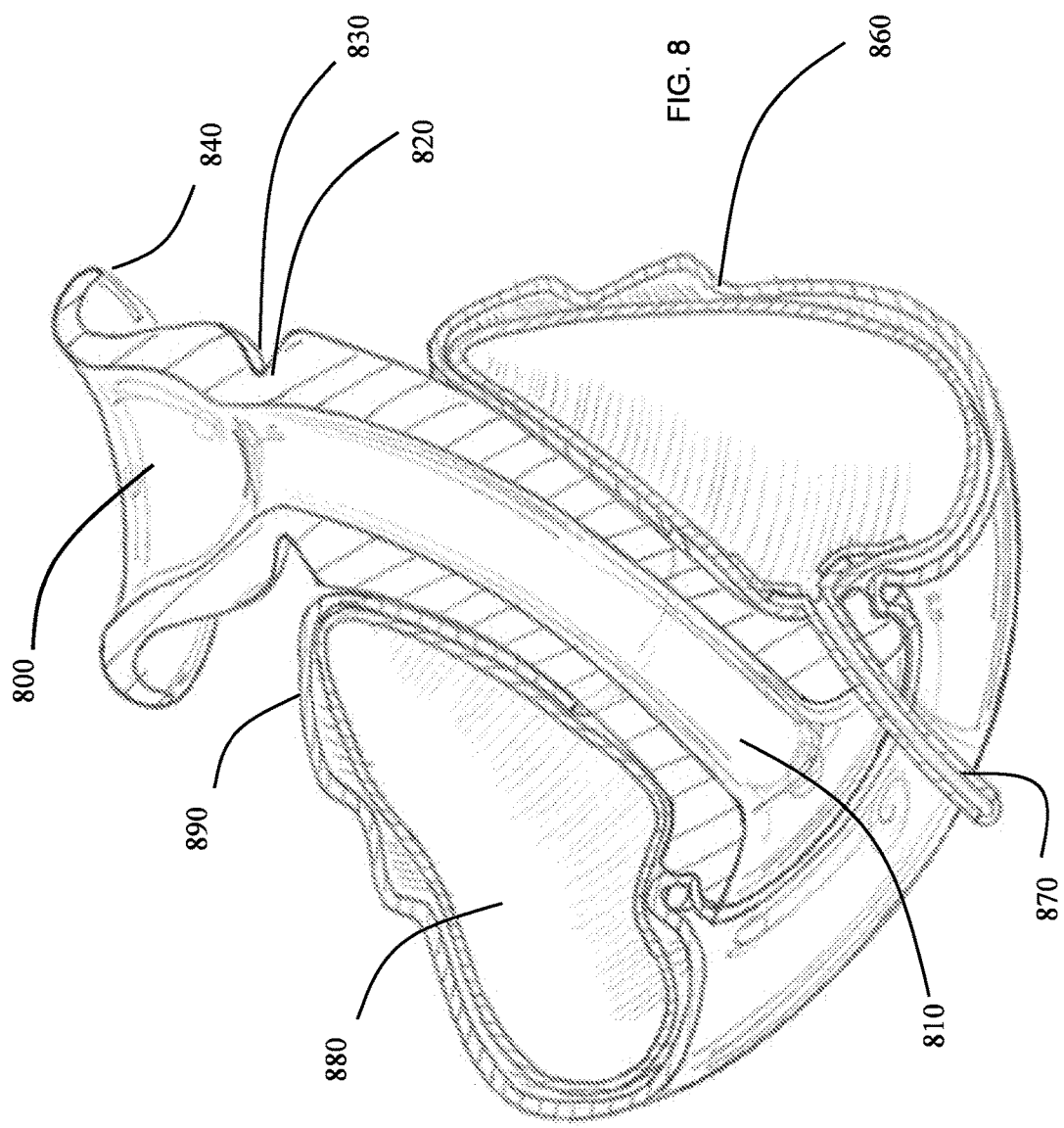
FIG. 8 is a cross section illustration of an embodiment of a cervical stabilization device comprising an inner and outer inflatable balloon structure.

FIG. 8 provides a cross-sectional view of another embodiment of a cervical stabilization device. As shown, cervical cup 800 is coupled to core portion 810 which allows for drainage of cervical fluids through vent opening 900 (shown in FIG. 10). In certain applications, it may be desirable to provide added flexibility of the core portion 810 to accommodate patient movement and provide ease of fitment in consideration of cervical tipping by coupling the cervical cup 800 to the core portion 810 using a flexural moment center 820 that allows for adjustment of the angle of the cervical cup 800 relative to the core portion 810. While the flexural moment center 820 may comprise any suitable structure that allows for such flexion of the juncture at which the cervical cup 800 and core portion 810 are coupled, in one embodiment, this may be accomplished by a concave core portion contour 830.

Figure 13:
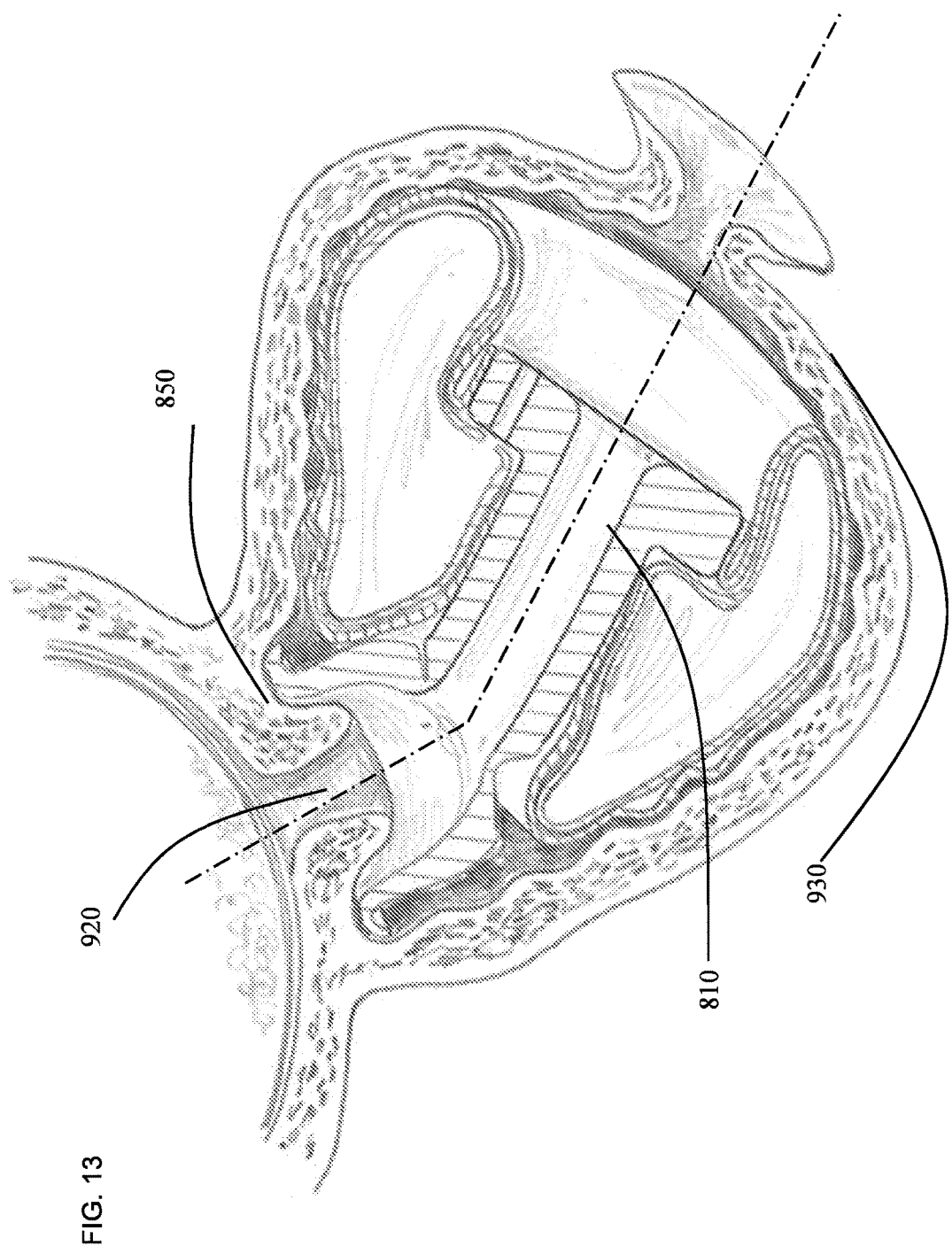

As depicted in FIGS. 8-13, cervical cup 800 may comprise a tapered or otherwise protruding cervical cup lip 840 which provides precise and delicate contact with the cervical fornices 850 of the cervix 920 (shown in FIG. 13). Thus, when properly seated, the cervical cup lip 840 at least partially surrounds the cervix while the void of the cervical cup itself does not engage the outer surface of the cervix between the entry of the cervix into the vagina and the opening of the cervical canal. The core portion 810 is at least partially surrounded by a bladder portion 860 which may be partially or fully inflated with a fluid through inflation valve 870. In some embodiments, the bladder portion 860 may comprise a single balloon and in other embodiments, a double-balloon structure comprising an inner 880 and outer balloon 890 may be preferable. In some embodiments, the bladder portion 860 may comprise a single balloon made of a polymer such as medical grade polyurethane and in other embodiments the bladder portion 860 may comprise a multiple layer balloon that may include an inner polyurethane portion and outer silicone portion.

The use of an inner 880 and outer balloon 890 rather than a single balloon to form the bladder portion 860 offers a greater array of options for materials that may comprise the balloons. For example, in some embodiments, the inner balloon 880 may be comprised of a polymer such as latex, polyurethane or any other suitable material that has a lower gas permeability effect, for example, a gas permeability effect that is less than or equal to 30 in units of $10^8$ $cm^2/(sec \cdot atm)$. The outer balloon 890 may then be comprised of a medical grade material, such as for example, silicone, which has a significantly higher gas permeability effect (390 in $10^8$ $cm^2/(sec \cdot atm)$) without resulting in deflation of the overall bladder portion 860 because the inner balloon 880 remains inflated despite the fact that the outer balloon 890 has such a high gas permeability that it would be unable to maintain the desired state of inflation. In embodiments in which a single balloon is used to form the bladder portion 860, a less gas permeable material capable of better restricting passage of the inflation fluid may be coated with a medical grade material such as silicone to allow for medical grade materials to remain in contact with the patient while still protecting against undesired deflation of the bladder portion 860.

Figure 9:
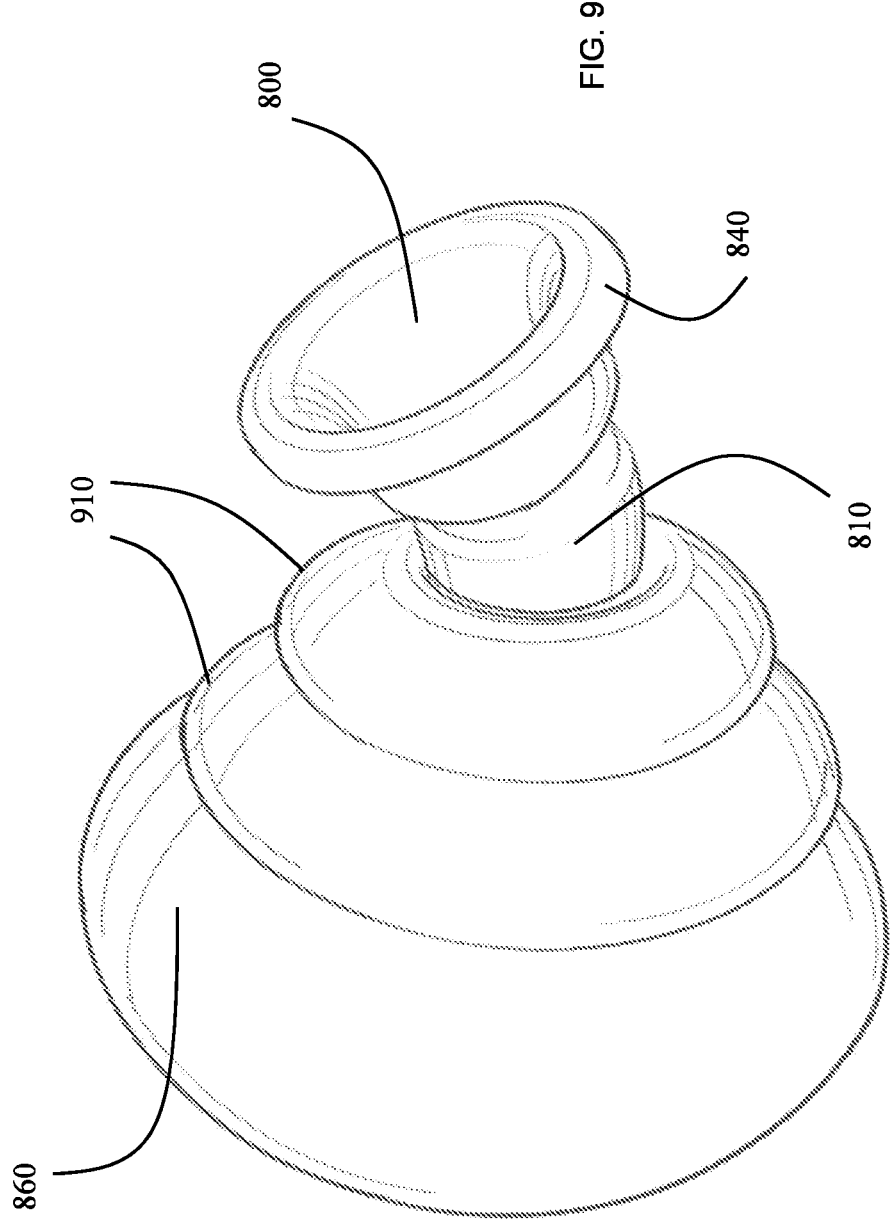
FIGS. 9-10 are perspective views of embodiments of a cervical stabilization device.
Figure 10:
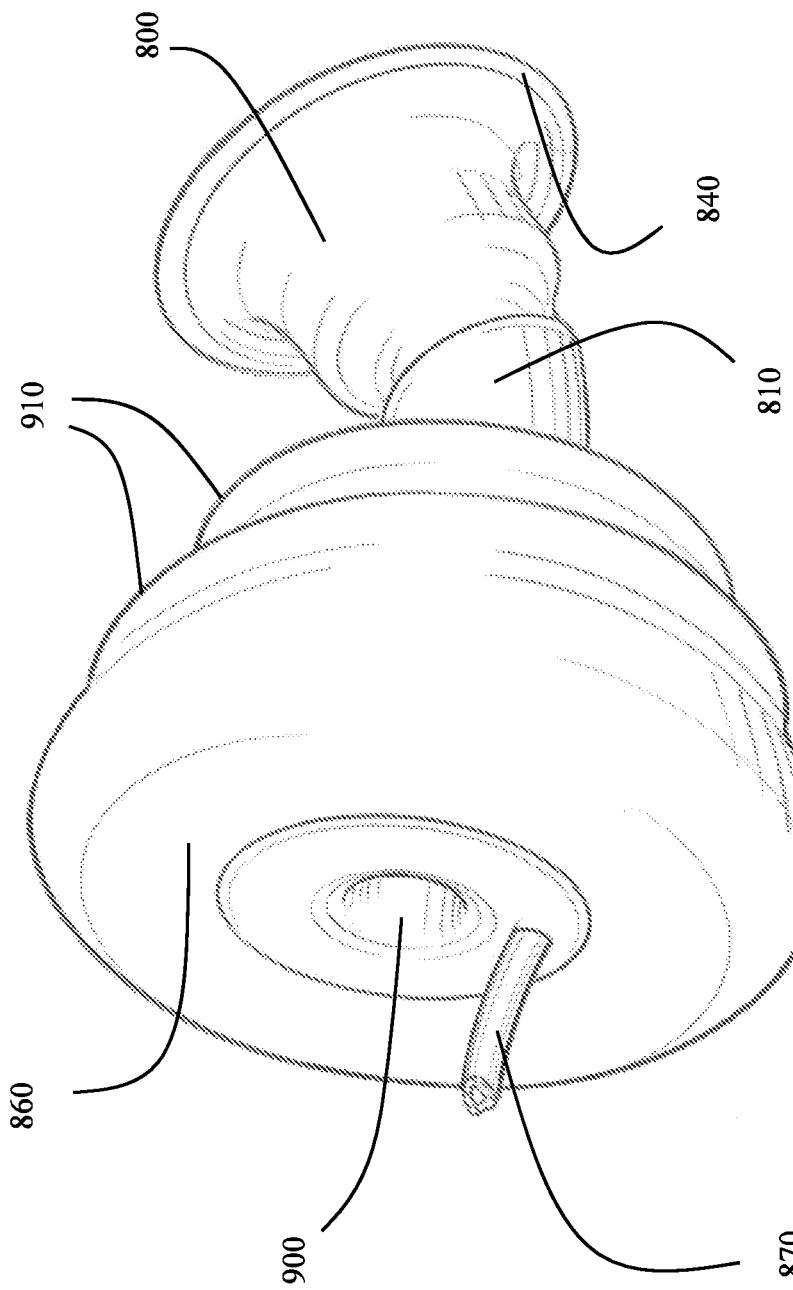

Regardless of whether a single or double balloon structure is used for the bladder portion 860, in some embodiments of the cervical stabilization device, it may be desirable to extend the core portion 810 at least partially beyond the bladder portion 860 so that the cervical cup 800 is not in contact with the bladder portion 860 when the bladder portion 860 is inflated. This reduces inadvertent stimulation of the delicate and highly reactive cervix resulting from pressure being applied to the cervical cup 800 when the bladder portion 860 is inflated. As shown in FIGS. 8-10, when the bladder portion 860 is inflated, even when the cervical cup 800 is located at an angle relative to the core portion 810, the inflated bladder portion 860 is not in contact with any portion of the cervical cup 800.

Figure 11:
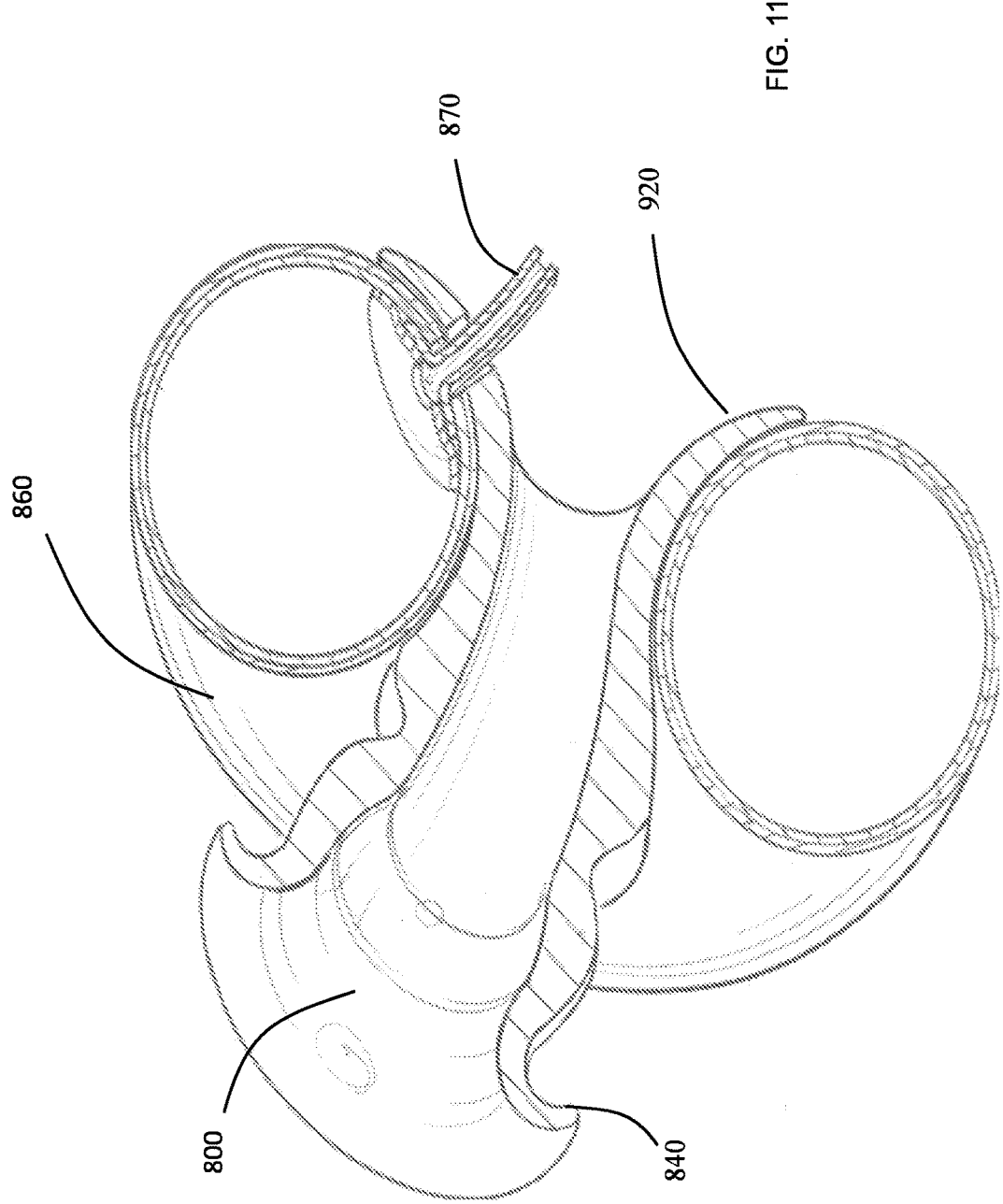
FIGS. 11-13 are cross section illustrations of various embodiments of a cervical stabilization device.
Figure 12:
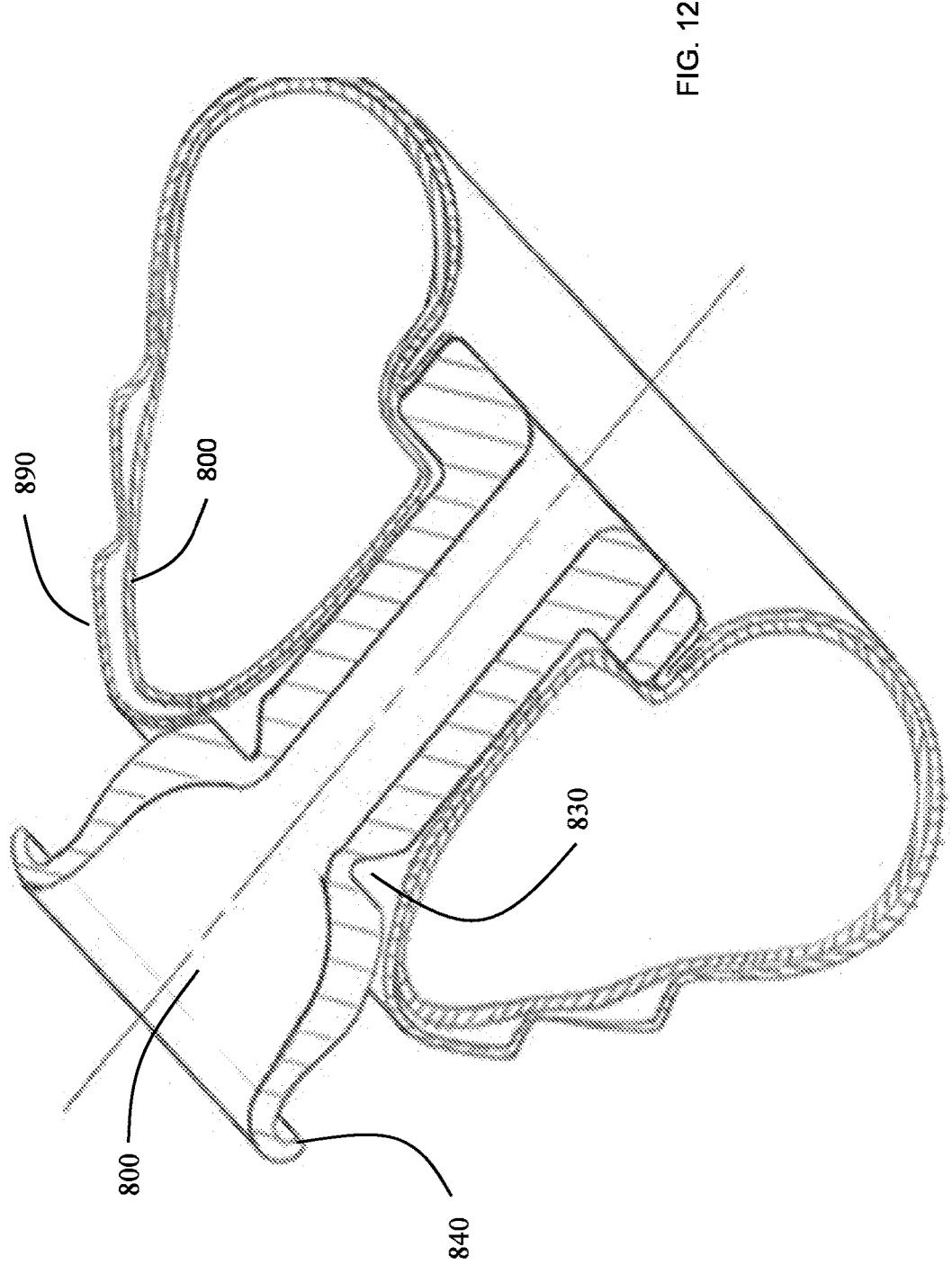

As shown in FIGS. 9-10, in some embodiments, the outer surface of the bladder portion 860 may further comprise one or more cleats 910 which are configured to engage with at least of portion of the vaginal wall when the cervical stabilization device is in use. Some embodiments may further comprise a pelvic floor seat 920, as shown in FIG. 11, which may extend at least partially under the lower portion of the bladder portion 860 and may assist in retaining the cervical stabilization device within the vaginal cavity as it rests upon the pelvic floor 930 (as shown in FIG. 13).

Figure 14:
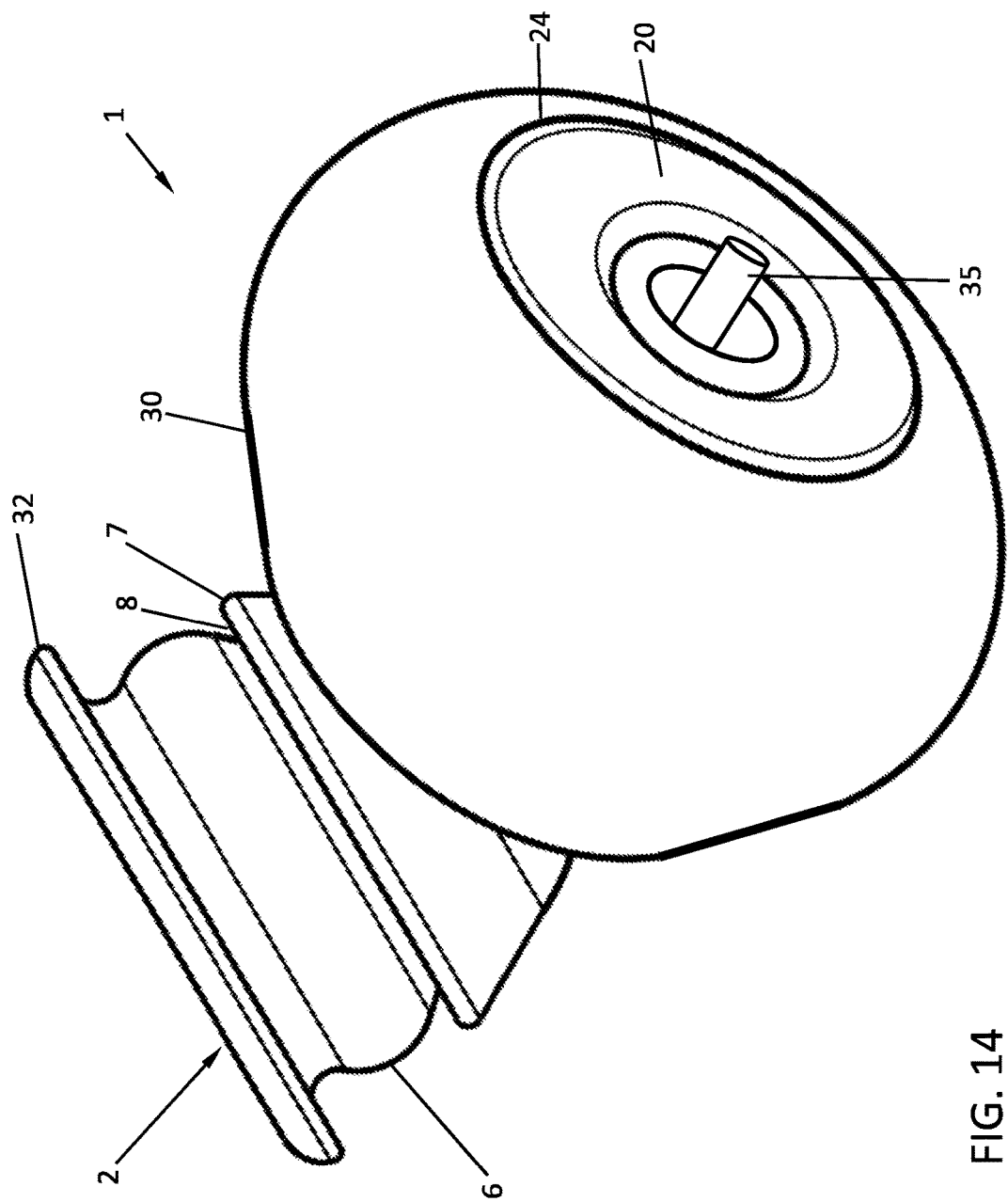
FIG. 14 is a perspective view of a first additional embodiment of a cervical stabilization device.
Figure 15:
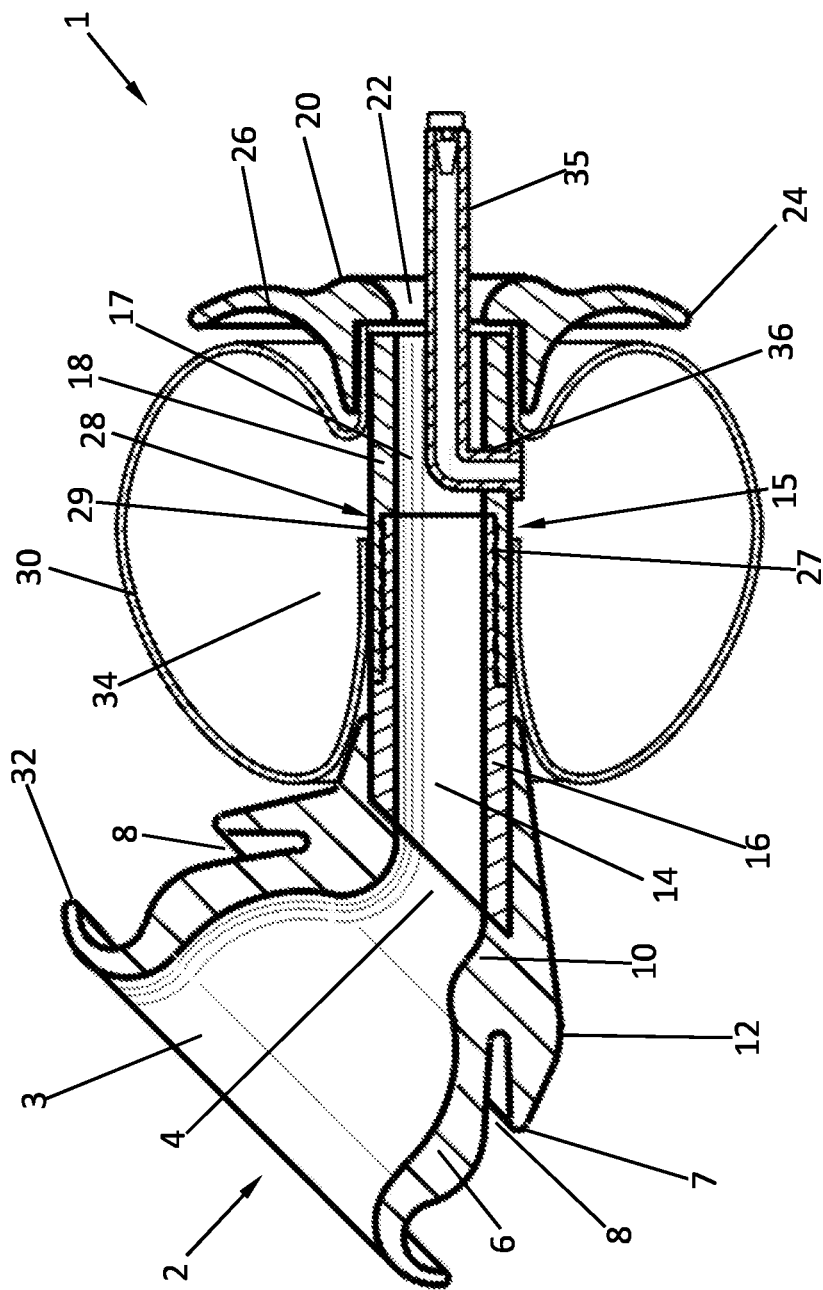
FIG. 15 is a cross section illustration of the first additional embodiment of a cervical stabilization device of FIG. 14.

FIGS. 14-15 depict another non-limiting embodiment of a cervical stabilization device 1. According to some aspects, a cervical stabilization device 1 comprises a cervical cup 2, an upper core tube 16 coupled or integrally formed with the cervical cup 2, a lower core tube 18 threadedly or otherwise adjustably coupled to the upper core tube 16 opposite the cervical cup 2, and an end cushion 20 coupled to the lower core tube 18 opposite the upper core tube portion 16.

Like other cervical cups described herein, the cervical cup 2 is configured to isolate and protect the uterine cervix. Embodiments of a cervical cup 2 may be made of any suitable medical grade material, such as but not limited to silicone having a durometer hardness of 30 to 70, Shore A. Moreover, embodiments of a cervical cup 2 may be manufactured by injection or resin transfer molding, casting, or any other suitable method of manufacture known in the art or described elsewhere in this document.

Similar to other cervical cups described herein, a cervical cup 2 may comprise a void 3 and a cervical cup lip 32. According to some aspects, a cervical cup lip is tapered or otherwise protruding from the cervical cup 2, which provides precise and delicate contact with the cervical fornices of the cervix. Thus, when properly seated, the cervical cup lip 32 of a cervical cup 2 at least partially surrounds the cervix while the void 3 of the cervical cup 2 does not engage the outer surface of the cervix between the entry of the cervix into the vagina and the opening of the cervical canal. The cervical cup lip 32 may, therefore, be positioned to gently contact and conform to the posterior and anterior cervical fornices. One or more embodiments of a cervical cup 2 further comprise a cervical cup sidewall 6 bordering the void 3 of the cervical cup 2. According to some aspects, the cervical cup sidewall 6 is configured to provide stiffness to the cervical cup 2 to prevent distortion of the cervical cup 2. A cervical cup 2 may further comprise at least one of a groove 8 around a base 10 of the cervical cup 2 and a lower lip 7 around the base 10 of the cervical cup 2. According to some aspects, a groove 8 is positioned adjacent a lower lip 7 to prevent or otherwise inhibit over-deflection of the cervical cup 2 respective to the position of the core tube.

A cervical cup 2 may further comprise a vent 4 at a base 10 of the cervical cup 2. The vent 4 is in fluid communication with the void 3 of the cervical cup 2, as well as fluid communication with the core tube passage of the core tube assembly. In one or more embodiments, a cervical cup 2 is angled relative to a core tube portion of the cervix support device 1. That is, a vent 4 and a void 3 of the cervical cup 2 may be angled at a different direction than the core tube passage of the core tube assembly. According to some aspects, a vent 4 of the cervical cup 2 and a core tube passage of the core tube assembly form an obtuse angle. More particularly, a vent 4 of the cervical cup 2 and a core tube passage of the core tube assembly may form an angle greater than 135 degrees. One or more embodiments further comprise an anterior stiffening shoulder 12 positioned on an outside of the obtuse angle formed by the vent 4 and the core tube passage. The anterior stiffening shoulder 12 is configured to assure proper positioning of the cervical cup 2 respective to the position of the core tube assembly.

As previously noted, a cervical cup 2 is coupled to or integrally formed with a core tube assembly 15. When in use, the core tube assembly 15 forms a bridge between the cervical cup 2 and an end cushion 20 to resist bearing forces acting upon the uterine cervix in opposition to the tissues of the pelvic floor. The core tube assembly 15 is further configured to allow for natural ventilation and drainage, as well as practitioner observation of the uterine cervix. In some embodiments, a core tube assembly 15 comprises a first or upper core tube 16 coupled to or integrally formed with a cervical cup 2 and a second or lower core tube 18 coupled to the upper core tube 16 opposite the cervical cup 2. The upper core tube 16 and the lower core tube 18 may be formed of any suitable material, including but not limited to polycarbonate, hard rubber or other suitable plastics or elastomers.

An upper core tube 16 may be at least partially positioned and coupled within a receiver on a base 10 of the cervical cup 2. In some embodiments, a portion of the upper core tube 16 is integrally molded into the receiver of the cervical cup 2 by a two-shot process that brings together the two unlike polymers in a co-forming process. In other embodiments, a portion of the upper core tube 16 is coupled within the receiver of the cervical cup 2 by any bonding technique known in the art, such as but not limited to adhesives, ultrasonic welding, silicone tape, and the like. The upper core tube 16 further comprises a first core tube passage 14 in fluid communication with the vent 4 of the cervical cup 2.

In one or more embodiments, a core tube assembly 15 is adjustable in length via an adjustable coupling of the upper core tube 16 and the lower core tube 18. More particularly, the adjustable coupling of a core tube assembly 15 may comprise but is not limited to an adjustable threaded coupling 28. An adjustable threaded coupling 28 allows for length adjustment of the core tube assembly 15 to meet the specific needs of the user. In such embodiments, an upper core tube 16 comprises threaded portion 27 that adjustably and threadedly couples to a threaded portion 29 of the lower core tube 18. In the non-limiting embodiment depicted in FIGS. 14-15, the threaded portion 27 of the upper core tube 16 comprises a male threaded portion 27, while the threaded portion 29 of the lower core tube 18 comprises a female threaded portion 29. Accordingly, a portion of the upper core tube 16 fits within the lower core tube 18 in some embodiments. It is contemplated, however, that in other embodiments the threaded portion of the upper core tube 16 may comprise a female threaded portion, while the threaded portion of the lower core tube 18 may comprise a male threaded portion. The adjustable feature described above may also be accomplished by other geometric treatments to the two or more core tube portions, such as but not limited to interlocking ring and groove, post and hole or other such mating configurations.

In addition, adjustably coupling to an upper core tube 16, a lower core tube 18 of a core tube assembly 15 may comprise a second core tube passage 17 in fluid communication with a first core tube passage 14 of the upper core tube 16. As described above, alignment of the core tube passages 14, 17 with the vent 4 allows for natural ventilation and drainage. A lower core tube 18 or an upper core tube 16 may further comprise a valve hole 36 configured to receive an inflation stem 35 and allow for inflation of the balloon 30. In FIG. 15, the valve hole 36 extends through the lower core tube 18 and the inflation stem 35 is plugged with a removable plug.

One or more embodiments of a cervical stabilization device 1 further comprise a flanged end cushion 20 coupled to or integrally formed with a lower core tube 18 opposite the upper core tube 16. The end cushion 20 may be made of any suitable medical grade material, such as but not limited to silicone or polyurethane having a durometer hardness of approximately 30 to 70, Shore A. The end cushion 20 may further be manufactured by any suitable manufacturing process, such as but not limited to injection or resin transfer molding, casting, and the like. In some embodiments, a portion of the lower core tube 18 is integrally molded into a receiver of the end cushion 20 by a two-shot process that brings together the two unlike polymers in a co-forming process. In other embodiments, a portion of the lower core tube 18 is coupled within a receiver of the end cushion 20 by any bonding known in the art, such as but not limited to adhesives, ultrasonic welding, silicone tape, and the like. According to some aspects, a portion of a balloon 30 is pinched or otherwise coupled between a portion of the end cushion 20 and a portion of the lower core tube 18.

Embodiments of an end cushion 20 comprise an opening 22 in fluid communication with the second core tube passage 17, and thus in fluid communication with the first core tube passage 14 and the vent 4. One or more embodiments of an end cushion 20 further comprise an annular cushion lip 24 around the opening 22. In more particular embodiments, an end cushion may comprise a recessed portion 26 facing inward towards the cervical cup 2 and positioned between the annular cushion lip 24 and the opening 22.

One or more embodiments of a cervical stabilization device 1 further comprise a balloon 30 coupled to the cervical stabilization device 1. The balloon 30 may be made of any suitable medical grade material or materials, such as but not limited to one or more outer layers comprising silicone and one or more inner layers of less permeable polyurethane. In other embodiments, the balloon may be made entirely of polyurethane or any other suitable elastopolymer. A balloon may be manufactured through any manufacturing process known in the art, such as but not limited to injection, resin transfer, blow molding, casting, and the like.

According to some aspects, a balloon 30 is coupled to a cervical stabilization device 1 to surround at least a portion of a core tube assembly 15, or at least a portion of a core tube assembly 15 may extend through a balloon 30. According to some aspects, a first end of a balloon is coupled proximate a first end of the lower core tube 16 and a second end of a balloon is coupled proximate a second end of the lower core tube 16, such as the non-limiting embodiment depicted in FIGS. 14-15. The balloon 30 may be coupled to the core tube assembly 15 with any coupling known in the art, such as but not limited to silicone tape, specialized adhesives, and the like. While a balloon 30 may be inflatable, it is further contemplated that the balloon 30 may comprise an outer skin of medical grade polyurethane, or silicone may encase a foam-like material to avoid inflation of the balloon. In such embodiments, the foam may be compressed manually or by vacuum before being positioned.

As noted above, a cervical stabilization device 1 may further comprise an inflation stem 35 configured to inflate the balloon 30 by filling the inner chamber 34 of the inflatable balloon with air (gas), liquid, gel, elastic foam or similar "memory materials", and the like or any combination thereof. According to some aspects, the inflation stem 35 extends through a valve hole 36 of a lower core tube 18, and then extends out of the second core tube passage 17 and opening 22 of the end cushion 20 to allow a user to inflate and/or deflate the inflatable balloon from outside the cervical stabilization device 1. Various valves, such as but not limited to a duckbill valve maybe inserted into the inflation stem 35 or used in association with the inflation stem to inflate the balloon 30 without departing from the scope this disclosure. A hand-held or any other suitable pump, a charged canister system, and the like may be utilized to inflate the balloon 30 via the valve stem 35. The balloon 30 may be deflated by removing the plug and/or valve within the plug or, in the case of memory materials, by vacuum or manual compression.

Figure 16:
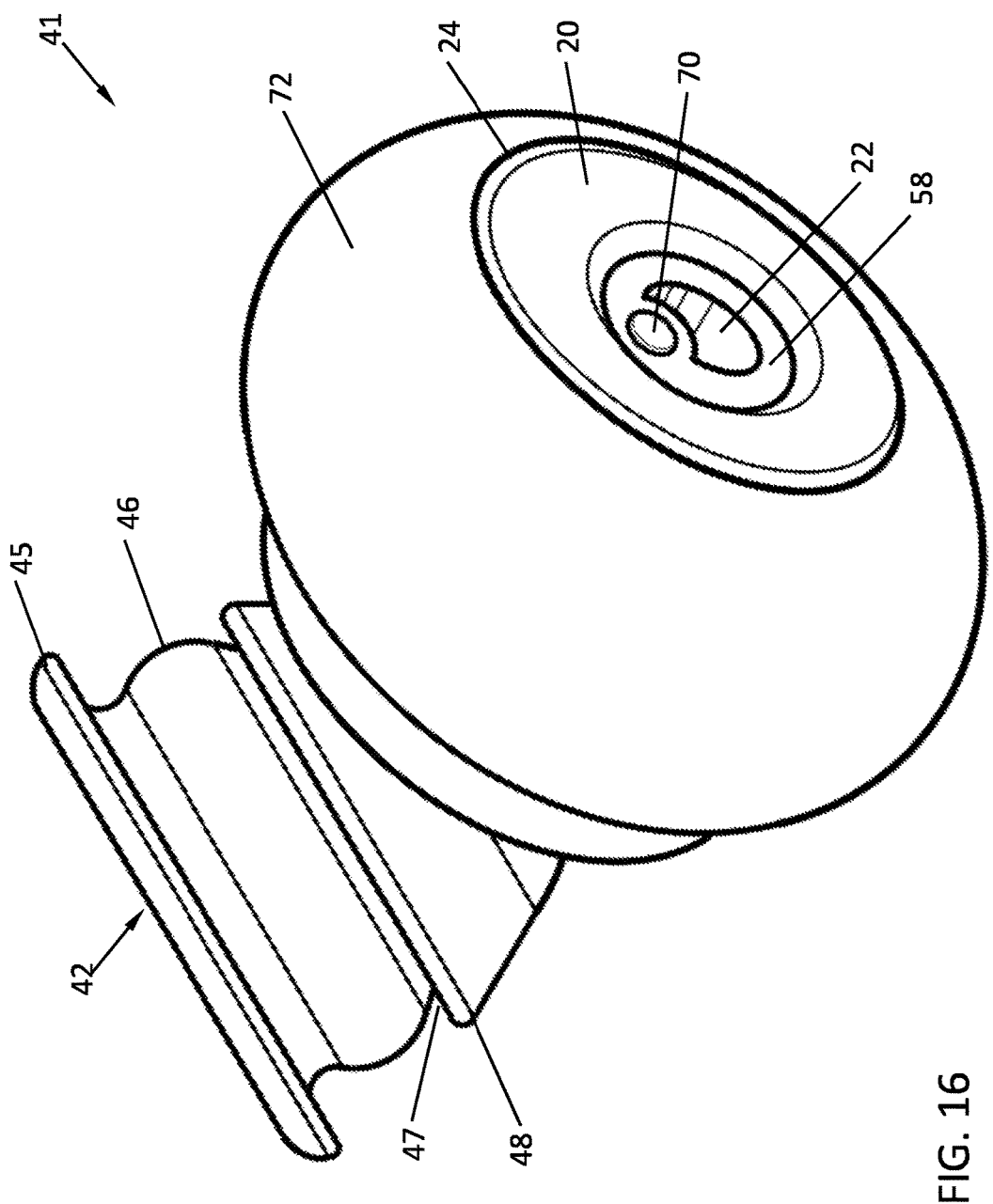
FIG. 16 is a perspective view of a second additional embodiment of a cervical stabilization device.
Figure 17:
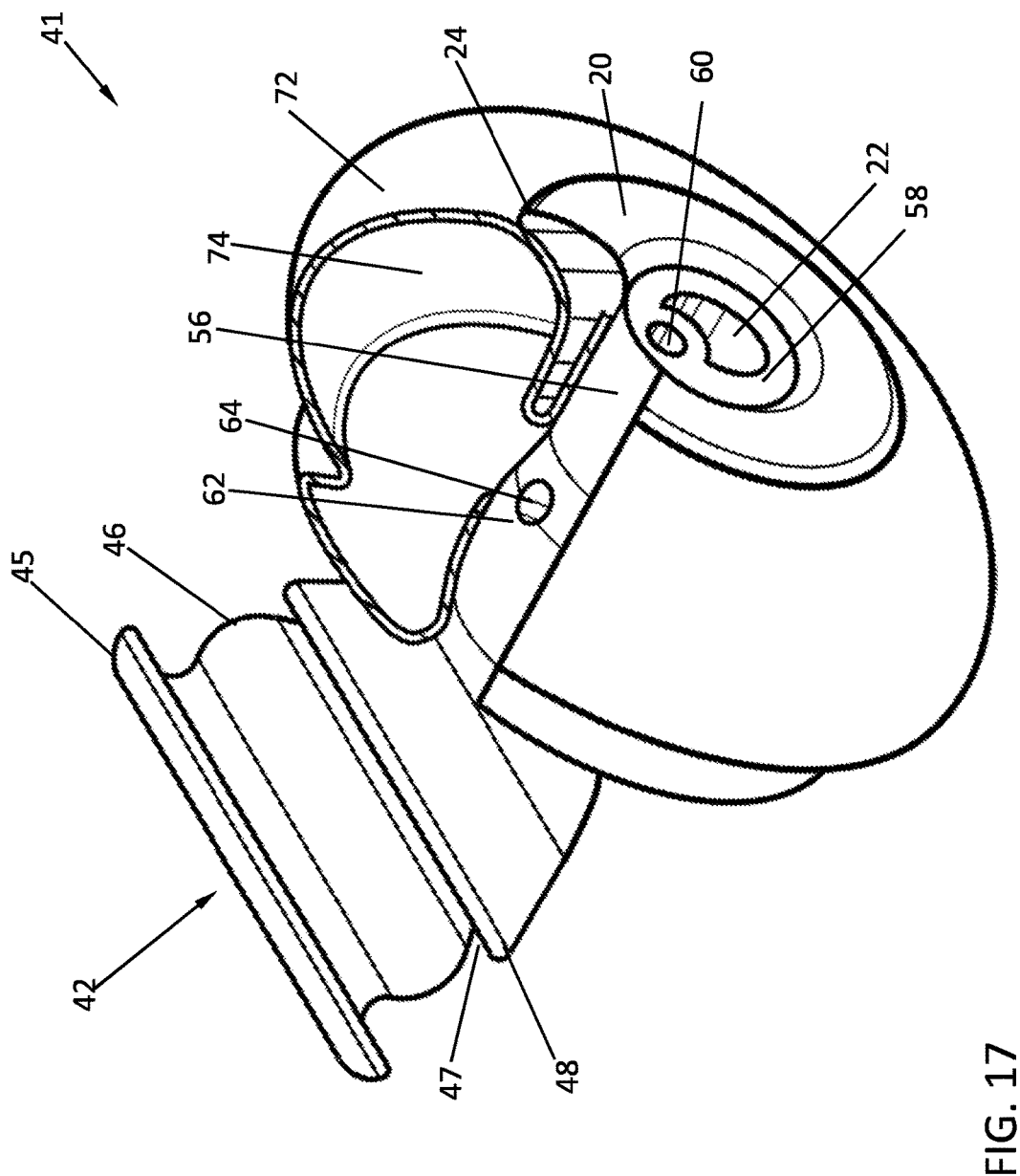
FIG. 17 is a perspective view of the second additional embodiment of a cervical stabilization device of FIG. 16 with a portion of the inflatable balloon removed.

FIGS. 16-19 depict another embodiment of a cervical stabilization device 41. Specifically, FIG. 16 provides a perspective view of a cervical stabilization device 41 with an inflatable balloon 72 inflated, FIG. 17 provides a perspective view of a cervical stabilization device 41 with an inflatable balloon 72 inflated with a portion of the inflatable balloon 72 being removed to allow viewing of the core tube 56, FIG. 18 provides an exploded cross sectional view of a cervical stabilization device without the inflatable balloon 72, and FIG. 19 provides a rear view of a cervical stabilization device 41. A cervical stabilization device 41 may comprise any of the features and functions described herein, and may be further utilized as a treatment of women's urinary incontinence and pelvic organ prolapse. According to some aspects, a cervical stabilization device 41 comprises a cervical cup 42, a core tube 56 integral with the cervical cup 42, and an end cushion 20 coupled to the core tube 56 opposite the cervical cup 42. Like other cervical cups described herein, the cervical cup 42 is configured to isolate and protect the uterine cervix. Embodiments of a cervical cup 42 may be made of any suitable medical grade material, such as but not limited to silicone having a durometer hardness of 30 to 70, Shore A. Moreover, embodiments of a cervical cup 42 may be manufactured by injection or resin transfer molding, casting, or any other suitable method of manufacture known in the art or described elsewhere in this document.

Similar to other cervical cups described herein, a cervical cup 42 may comprise a void 43 and an upper cervical cup lip 45. According to some aspects, a cervical cup lip 45 is tapered or otherwise protruding from the cervical cup 42, which provides precise and delicate contact with the cervical fornices of the cervix. Thus, when properly seated, the upper cervical cup lip 45 of a cervical cup 42 at least partially surrounds the cervix while the void 43 of the cervical cup 42 does not engage the outer surface of the cervix between the entry of the cervix into the vagina and the opening of the cervical canal. The upper cervical cup lip 45 may, therefore, be positioned to gently contact and conform to the posterior and anterior cervical fornices. One or more embodiments of a cervical cup 42 further comprise a cervical cup sidewall 46 bordering the void 43 of the cervical cup 42. According to some aspects, the cervical cup sidewall 46 is configured to provide stiffness to the cervical cup 42 to prevent distortion of the cervical cup 42. A cervical cup 42 may further comprise at least one of a groove 47 around a base 50 of the cervical cup 42 and a lower lip 48 around the base 50 of the cervical cup 42. According to some aspects, a groove 47 is positioned adjacent a lower lip 48 to prevent or otherwise inhibit over-deflection of the cervical cup 42 respective to the position of the core tube.

A cervical cup 42 may further comprise a vent 44 at a base 50 of the cervical cup 42. The vent 44 is in fluid communication with the void 43 of the cervical cup 42, as well as fluid communication with the core tube passage 54 of the core tube 56. In one or more embodiments, a cervical cup 42 is angled relative to a core tube 56 of the cervix support device 41. That is, a vent 44 and a void 43 of the cervical cup 42 may be angled at a different direction than the core tube passage 54 of the core tube 56. According to some aspects, a vent 44 of the cervical cup 42 and a core tube passage 54 of the core tube 56 form an obtuse angle. More particularly, a vent 44 of the cervical cup 42 and a core tube passage 54 of the core tube 56 may form an angle greater than 135 degrees. One or more embodiments further comprise an anterior stiffening shoulder 52 positioned on an outside of the obtuse angle formed by the vent 44 and the core tube passage 54. The anterior stiffening shoulder 52 is configured to assure proper positioning of the cervical cup 42 respective to the position of the core tube assembly.

As previously noted, a cervical cup 42 may be integrally formed with a core tube 56. The core tube 56 comprises a wall 62 configured to prevent unwanted bending of the core tube 56 and resist bearing forces acting upon the uterine cervix in opposition to the tissues of the pelvic floor. The core tube 56 further comprises a core tube passage 54 in fluid communication with the vent 44 of the cervical cup 42. The core tube 56 is configured to allow for natural ventilation and drainage, as well as practitioner observation of the uterine cervix. The core tube 56 may be formed of any suitable material, including but not limited to polycarbonate, hard rubber, or other suitable plastics or elastomers.

According to some aspects a cervical stabilization device 41 comprises an inflation passage 60 within a wall 62 of the core tube 56. The inflation passage 60 may extend from an end opening 68 opposite the cervical cup 42 to a wall opening 64 on the wall 62 of the core tube 56. More particularly, the wall opening 64 may be positioned between a terminating end 58 of the core tube 56 and the cervical cup 42. One or more embodiments of a cervical stabilization device 41 further comprise an inflation valve 66 positioned within the inflation passage 60. The inflation valve 66 may comprise any inflation valve known in the art, such as but not limited to a duckbill inflation valve. One or more embodiments may also comprise a sealing plug 70 coupled to the end opening 68 of the inflation passage 60 and configured to plug the end opening 68. The sealing plug 70 is accessible outside the end cushion 20 according to some embodiments. It is contemplated that although an inflation passage 60, inflation valve 66, and sealing plug 70 are depicted with a cervical stabilization device 41, one or more of these may be utilized with any other cervical stabilization devices disclosed herein without departing from the scope of this disclosure.

One or more embodiments of a cervical stabilization device 41 further comprise a flanged end cushion 20 similar to an end cushion 20 described elsewhere in this document. The end cushion 20 may be coupled to or integrally formed with a core tube 56 opposite the cervical cup 42. In some embodiments, a portion of the core tube 56 is integrally molded into a receiver of the end cushion 20 by a two-shot process that brings together the two unlike polymers in a co-forming process. In other embodiments, a portion of the core tube 56 is coupled within a receiver of the end cushion 20 by any bonding known in the art, such as but not limited to adhesives, ultrasonic welding, silicone tape, and the like. According to some aspects, a portion of a balloon 72 is pinched or otherwise coupled between a portion of the end cushion 20 and a portion of the core tube 56.

Embodiments of an end cushion 20 comprise an opening 22 in fluid communication with the second core tube passage 54, and thus in fluid communication with the vent 44. One or more embodiments of an end cushion 20 further comprise an annular cushion lip 24 around the opening 22. In more particular embodiments, an end cushion may comprise a recessed portion 26 facing inward towards the cervical cup 42 and positioned between the annular cushion lip 24 and the opening 22.

One or more embodiments of a cervical stabilization device 41 further comprise a balloon 72 coupled to the cervical stabilization device 41. The balloon 72 may be similar to any other inflatable balloons described herein, such as but not limited to inflatable balloon 30. Accordingly, a balloon 72 may be made of any suitable medical grade material or materials, such as but not limited to one or more outer layers comprising silicone and one or more inner layers of less permeable polyurethane. In other embodiments, the balloon may be made entirely of polyurethane or any other suitable elastopolymer. A balloon may be manufactured through any manufacturing process known in the art, such as but not limited to injection, resin transfer, blow molding, casting, and the like.

According to some aspects, a balloon 72 is coupled to a cervical stabilization device 41 to surround at least a portion of a core tube 56, or at least a portion of a core tube 56 may extend through a balloon 72. More particularly, an inflatable balloon 72 surrounds the core tube 56 and is positioned such that an inner chamber 74 of the inflatable balloon 72 is in fluid communication with the inflation passage 60 and the inflatable balloon 72 does not extend beyond the lower lip 48 of the cervical cup 42 when the inflatable balloon 72 is inflated. According to some aspects, a first end of a balloon is coupled proximate a first end of the core tube 56 proximate the cervical cup 42 and a stem 76 or second end of a balloon 72 is coupled proximate a terminating end 58 of the core tube 56, such as the non-limiting embodiment depicted in FIGS. 16 and 17. The balloon 72 may be coupled to the core tube 56 with any coupling known in the art, such as but not limited to silicone tape, specialized adhesives, ultrasonic welding and the like. A balloon 72 may be inflated or deflated as described elsewhere in this document. For example, a hand-held or any other suitable pump, a charged canister system, and the like may be utilized to inflate the balloon 72 via the inflation passage 60. The balloon 72 may be deflated by removing the plug and/or valve within the plug or, in the case of memory materials, by vacuum or manual compression.

Figure 20:
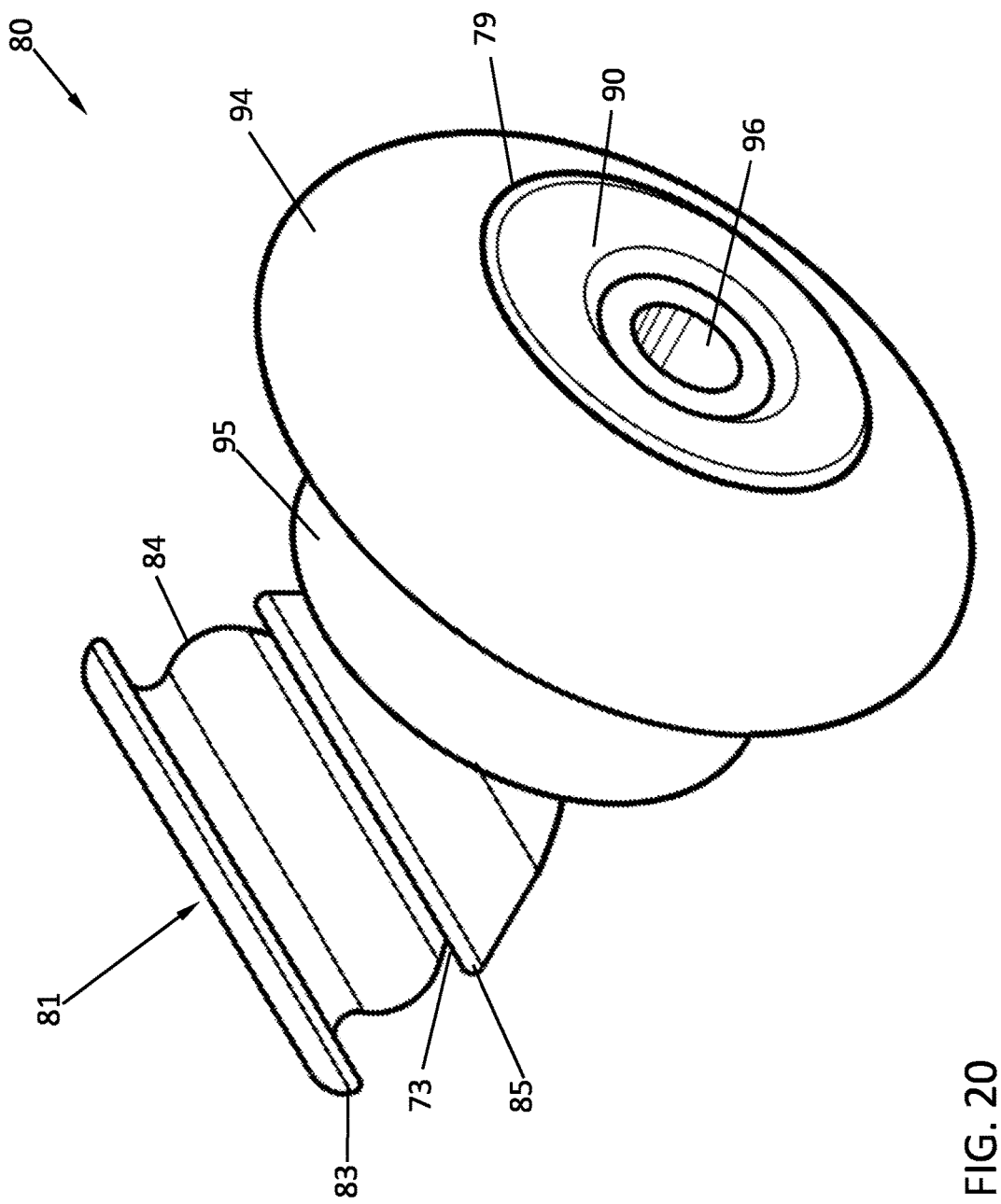
FIG. 20 is a perspective view of a third additional embodiment of a cervical stabilization device.
Figure 21:
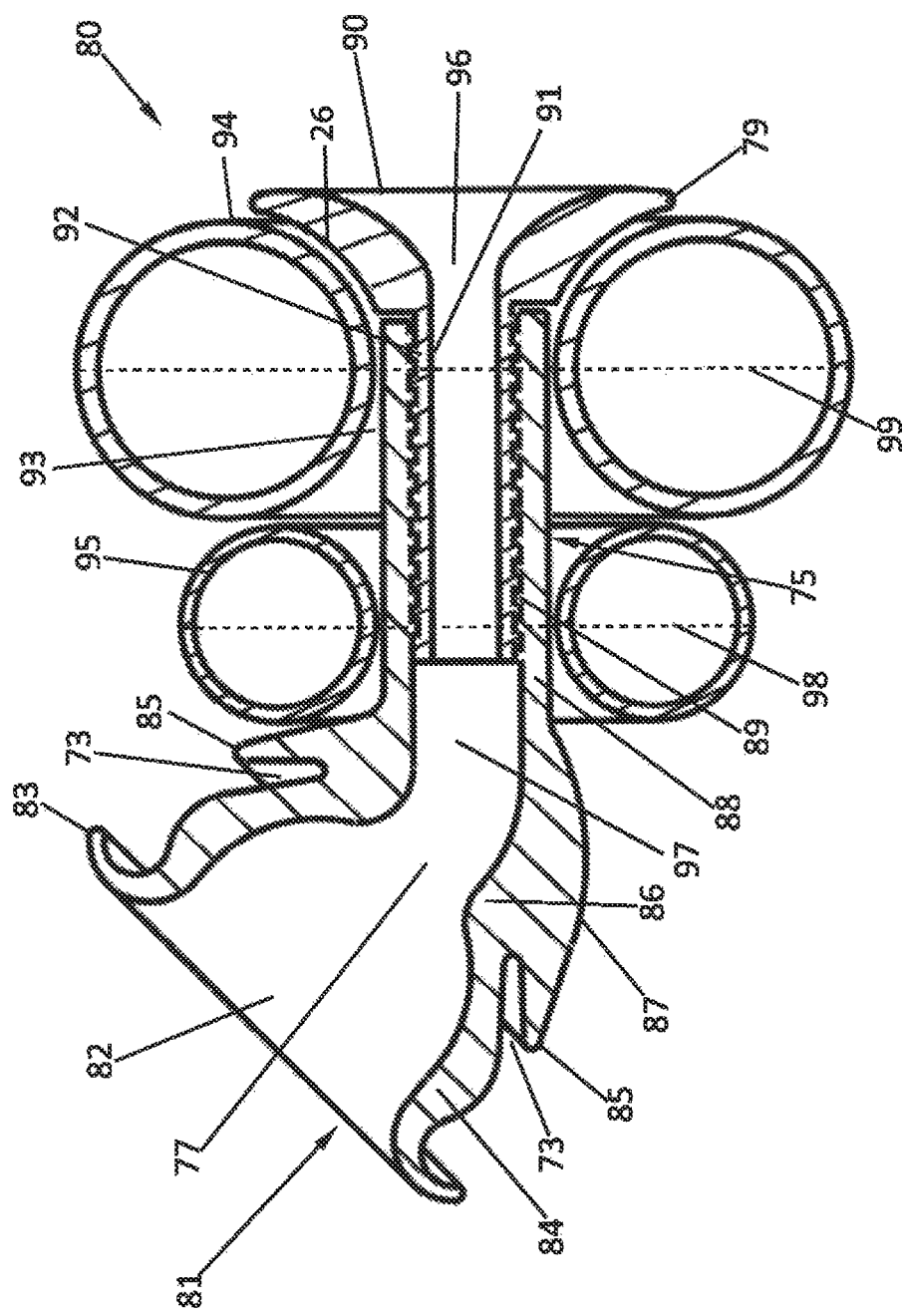
FIG. 21 is a cross section illustration of the third additional embodiment of a cervical stabilization device of FIG. 20.
Figure 22:
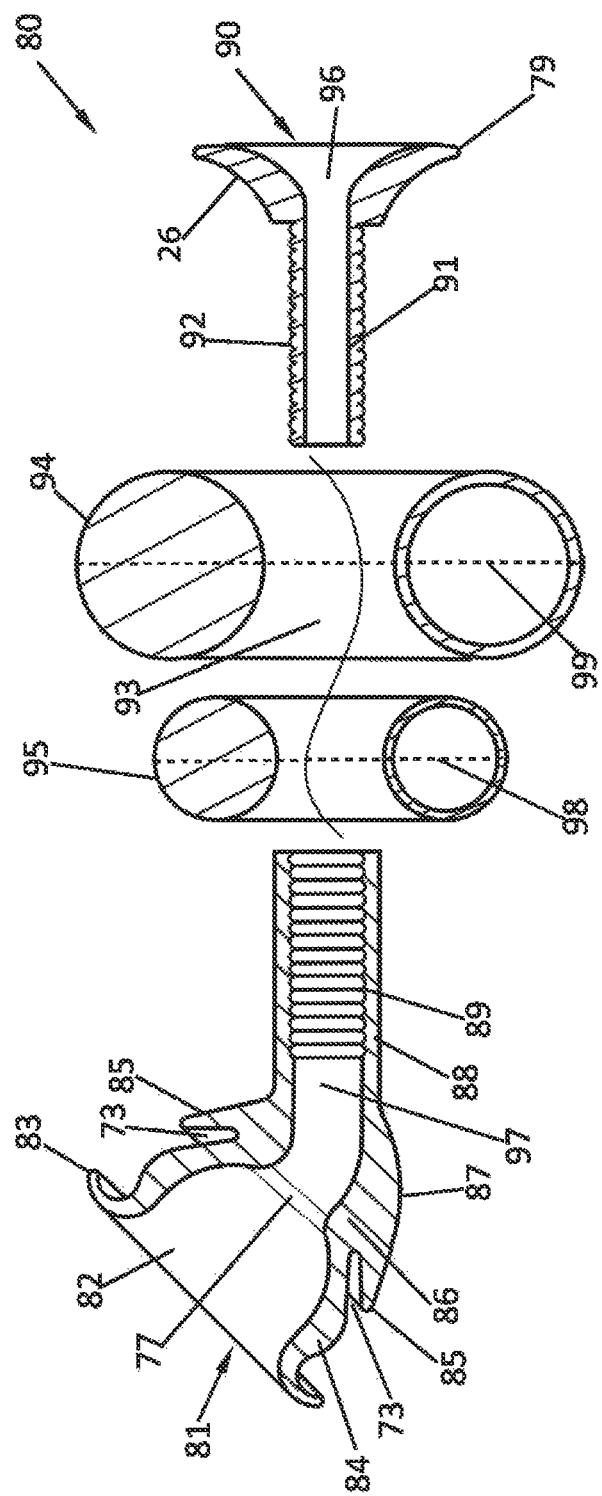
FIG. 22 is an exploded cross section illustration of the third additional embodiment of a cervical stabilization device of FIG. 20.

FIGS. 20-22 depict another embodiment of a cervical support device 80. Specifically, FIG. 20 depicts a perspective view of a cervical support device 80, FIG. 21 depicts a cross-sectional view of the cervical support device of FIG. 20, and FIG. 22 depicts an exploded cross-sectional view of the cervical support device of FIG. 20. According to some aspects, a cervical stabilization device 80 comprises a cervical cup 81, core tube assembly 75 coupled or integrally formed with the cervical cup 81, and an end cushion 20 positioned opposite the cervical cup 81.

Like other cervical cups described herein, the cervical cup 81 is configured to isolate and protect the uterine cervix. Embodiments of a cervical cup 81 may be made of any suitable medical grade material, such as but not limited to silicone having a durometer hardness of 30 to 70, Shore A. Moreover, embodiments of a cervical cup 81 may be manufactured by injection or resin transfer molding, casting, or any other suitable method of manufacture known in the art or described elsewhere in this document.

Similar to other cervical cups described herein, a cervical cup 81 may comprise a void 82 and an upper cervical cup lip 83. According to some aspects, an upper cervical cup lip 83 is tapered or otherwise protruding from the cervical cup 81, which provides precise and delicate contact with the cervical fornices of the cervix. Thus, when properly seated, the upper cervical cup lip 83 of a cervical cup 81 at least partially surrounds the cervix while the void 82 of the cervical cup 81 does not engage the outer surface of the cervix between the entry of the cervix into the vagina and the opening of the cervical canal. The upper cervical cup lip 83 may, therefore, be positioned to gently contact and conform to the posterior and anterior cervical fornices. One or more embodiments of a cervical cup 81 further comprise a cervical cup sidewall 84 bordering the void 82 of the cervical cup 81. According to some aspects, the cervical cup sidewall 84 is configured to provide stiffness to the cervical cup 81 to prevent distortion of the cervical cup 81. A cervical cup 81 may further comprise at least one of a groove 73 around a base 86 of the cervical cup 81 and a lower lip 85 around the base 86 of the cervical cup 81. According to some aspects, a groove 73 is positioned adjacent a lower lip 85 to prevent or otherwise inhibit over-deflection of the cervical cup 81 respective to the position of the core tube 75.

A cervical cup 81 may further comprise a vent 77 at a base 86 of the cervical cup 81. The vent 77 is in fluid communication with the void 82 of the cervical cup 81, as well as fluid communication with the core tube passage 97 of the core tube assembly 75. In one or more embodiments, a cervical cup 81 is angled relative to a core tube assembly 75 of the cervical support device 80. That is, a vent 77 and a void 82 of the cervical cup 81 may be angled at a different direction than the core tube passage 97 of the core tube assembly 75. According to some aspects, a vent 77 of the cervical cup 81 and a core tube passage 97 of the core tube assembly 75 form an obtuse angle. More particularly, a vent 77 of the cervical cup 81 and a core tube passage 97 of the core tube assembly 75 may form an angle greater than 135 degrees. One or more embodiments further comprise an anterior stiffening shoulder 87 positioned on an outside of the obtuse angle formed by the vent 77 and the core tube passage 97. The anterior stiffening shoulder 87 is configured to assure proper positioning of the cervical cup 81 respective to the position of the core tube assembly 75.

As previously noted, a cervical cup 81 is coupled to or integrally formed with a core tube assembly 75. When in use, the core tube assembly 75 forms a bridge between the cervical cup 81 and an end cushion 90 to resist bearing forces acting upon the uterine cervix in opposition to the tissues of the pelvic floor. The core tube assembly 75 is further configured to allow for natural ventilation and drainage, as well as practitioner observation of the uterine cervix. In some embodiments, a core tube assembly 75 comprises a first or outer core tube 88 coupled to or integrally formed with a cervical cup 81 and a second or inner core tube 91 coupled to the outer core tube 88 opposite the cervical cup 81. In other embodiments, the first core tube 88 may comprise an inner core tube and the second core tube 91 may comprise an outer core tube. The outer core tube 88 and the inner core tube 91 may be formed of any suitable material, including but not limited to polycarbonate, hard rubber, or other suitable plastics or polymers. An outer core tube 88 may be integrally formed with the cervical cup 81, such as the non-limiting embodiment depicted in FIGS. 21-22. In other embodiments, the outer core tube 88 may be coupled to the cervical cup 81 similar to the upper core tube 16 and the cervical cup 2 described above. The outer core tube 88 further comprises a tube passage 97 in fluid communication with the vent 77 of the cervical cup 81.

One or more embodiments of a cervical stabilization device 80 further comprise a flanged, disc-like or bell-shaped end cushion 90 positioned opposite the cervical cup 81. According to some aspects, an inner core tube 91 is integral with or coupled to the end cushion 90. In the non-limiting embodiment depicted in FIGS. 21-22 the inner core tube 91 is integral with the end cushion 90. The end cushion 90 comprises an annular cushion lip 79 and an opening 96 extending through the annular lip 79 and the inner core tube 91 such that the opening 96 is in fluid communication with the tube passage 97 and the vent 77.

According to some aspects, the end cushion 90 is removably coupled to the outer core tube 88 with an interlocking or threaded configuration. In the non-limiting embodiment depicted in FIG. 21 a plurality of ribs 89 on an inner surface of the outer core tube 88 engage with a plurality of ribs 92 on an outer surface of the inner core tube 91 to removably couple the end cushion 90 to the outer core tube 88. This interlocking configuration between the inner core tube 91 and the outer core tube 88 eliminates the need for bonding during assembly of a cervical support device 80. In other embodiments, the inner core tube 91 may threadedly couple to the outer core tube 88, similar to the threaded coupling between the upper core tube 16 and the lower core tube 18 described above. Moreover, in particular embodiments, the outer core tube 88 is adjustably coupled to the inner core tube 91 such that a user or practitioner may adjust the length of the core tube assembly 75 to meet the specific needs of the user.

One or more embodiments of a cervical support device 80 further comprise at least one pessary ring. Although pessary rings are shown and described in relation to a cervical support device 81, it is contemplated that pessary rings may be utilized with other cervical support devices described herein without departing from the scope of this disclosure. According to some aspects, the pessary rings 94, 95 comprise a silicone or other suitable material having thicker skin portions and hollow interiors. Pessary rings eliminate the need to inflate a balloon, and a wide range of pessary rings may be arranged to meet the particular needs of an individual patient. For example, in the non-limiting embodiment depicted in FIGS. 21-22, a cervical support device 81 comprises a large pessary ring 94 having an outer diameter 99 and a small pessary ring 95 having an outer diameter 98 smaller than the outer diameter 99 of the large pessary ring 94. Although two pessary rings 94, 95 are shown in FIGS. 21-22, it is contemplated that cervical support devices 81 may include a single pessary ring, or greater than two pessary rings.

Each pessary ring 94, 95 comprises a ring opening 93 sized larger than an outer diameter of the outer core tube 88, but smaller than a diameter of the annular cushion lip 79 and the cervical cup 81 such that the cushion lip 79 and the cervical cup 81 inhibit removal of each pessary ring 94, 95 when the end cushion 90 is coupled to the outer core tube 88. More particularly, the ring opening 93 may be sized such that each pessary ring 94, 95 is held between the cushion lip 79 of the end cushion 90 and the lower lip 85 and anterior stiffening shoulder 87 of the cervical cup 81 when the end cushion 90 is coupled to the outer core tube 88.

While any of the disclosed embodiments may be comprised of more rigid materials, to ease in positioning of the cervical stabilization device and to accommodate patient movement as well as varying locations of the cervix among patients resulting from cervical tipping, it may be preferable for at least some of the components of the cervical stabilization device, such as for example, the inner and/or outer balloons in double balloon embodiments, a single balloon in single balloon embodiments, or the core portion to be comprised of a flexible material that has a hardness rating within a range of 30 to 60 durometer on the Shore A Scale, such as for example, medical grade silicone. In certain embodiments it may also be preferable to select a material of which the cervical cup is comprised to have a hardness rating within a range of 40 to 80 durometer on the Shore A Scale.

The various embodiments of the cervical stabilization device operate in a similar manner. The cervical stabilization device is inserted into the vagina. The cervix is surrounded by a nesting area or cervical cup of the cervical stabilization device. The cervical stabilization device is positioned such that the cervix is not engaged by the nesting area or cervical cup, so to lessen the amount of stimulation/disruption of the cervix. Discharges emanating from the cervical canal are drained through a vent in the nesting area or cervical cup. The uterine support shoulder or cervical cup lip of the cervical support device, which surrounds the nesting area or cervical cup, supports weight bearing down upon the cervix. The uterine support shoulder is coupled to a seat portion of the cervical stabilization device in some embodiments, and in other embodiments the cervical cup lip is coupled to a core portion that is at least partially surrounded by an inflatable bladder or 'balloon' portion. The seat portion or cleating on the outer surface of the bladder portion engages the vaginal wall, thus helping the uterine support shoulder to support the uterus. In an embodiment with an inflatable bladder, the bladder may be generally beneath the seat portion—serving to help engage the seat portion with the vaginal wall. The bladder may also function such as to reduce stimulation of the cervix by resisting the downward force upon the cervix as the uterus ripens, by disposing such bearing forces upon the resilient tissues of the vaginal wall (which may be aided by the seat portion) and by expanding to fill the vaginal cavity to such a degree as to extend the bladder to terminate opposing the tissues proximate the lower pelvic structure to resist displacement and expulsion of the device. Support of the uterus and protection/stabilization of the cervix is continuous for an extended period of time, such as the days, week or weeks that typically exist between office visits rather than merely the time during a particular office visit, or for so long as may be prescribed by the attending physician throughout specific stages of a troubled pregnancy.

It is important to note that all of the embodiments discussed above, as well as other implementations not specifically discussed in this description but which become apparent from this description when combined with the knowledge of one of ordinary skill in the art, may be customized to improve the fit of the device and comfort for a particular patient. The use of the device may also lead to the need for improved insertion, positioning, and extraction instruments to facilitate the utilization of the device and further enhance patient comfort.

The implementations listed here, and many others, will become readily apparent from this disclosure. From this, those of ordinary skill in the art will readily understand the versatility with which this disclosure may be applied. Implementations of a cervical stabilization device may be constructed of a wide variety of materials, including as described above. Those of ordinary skill in the art will readily be able to select appropriate materials and manufacture these products from the disclosures provided herein.

Some components defining a cervical stabilization device may be manufactured simultaneously and integrally joined with one another, while other components may be purchased pre-manufactured or manufactured separately and then assembled with the integral components. Various implementations may be manufactured using conventional procedures as added to and improved upon through the principles described here.

Accordingly, manufacture of these components separately or simultaneously may involve vacuum forming, injection molding, flow molding, blow molding, transfer molding, compression molding, milling, drilling, reaming, stamping, pressing, cutting and/or the like. Components manufactured separately may then be coupled or removably coupled with the other integral components in any manner, such as with adhesive, a weld joint, a fastener, any combination thereof, and/or the like for example, depending on, among other considerations, the particular material forming the components. Particular manufacturing techniques and materials are used in the medical industry for safety purposes and have been approved by the relevant authorities. It is anticipated that these approved materials and manufacturing techniques known in the art will be used in manufacturing the various implementations of cervical stabilization devices described in and apparent from this disclosure.

It will be understood that implementations are not limited to the specific components disclosed herein, as virtually any components consistent with the intended operation of a method and/or system implementation for a cervical stabilization device may be utilized. Accordingly, for example, although particular component examples may be disclosed, such components may comprise any shape, size, style, type, model, version, class, grade, measurement, concentration, material, weight, quantity, and/or the like consistent with the intended operation of a method and/or system implementation for a cervical stabilization device may be used.

In places where the description above refers to particular implementations of a cervical stabilization device, it should be readily apparent that a number of modifications may be made without departing from the spirit thereof and that these implementations may be applied to other cervical stabilization devices. The presently disclosed implementations are, therefore, to be considered in all respects as illustrative and not restrictive.

I claim:
1. A cervical support device comprising:
a cervical cup configured to receive a cervix extending from a uterus, the cervical cup comprising a void sized to surround an outer surface of the cervix, a vent, an upper lip proximate the void, and a lower lip extending from a base of the cervical cup;
a core tube fixedly joined to the cervical cup and comprising a core tube passage in fluid communication with the vent of the cervical cup;
an annular ring surrounding the core tube and removably mounted to the core tube and cervical cup; and
a flanged end cushion removably coupled to the core tube such that the annular ring is disposed between the flanged end cushion and the cervical cup and the flanged end cushion is in contact with the annular ring, the flanged end cushion comprising an opening in fluid communication with the core tube passage and a cushion lip surrounding the opening, the flanged end cushion retaining the annular ring on the core tube when the flanged end cushion is coupled to the core tube and wherein when the flanged end cushion is removed from the core tube, the annular ring surrounding the core tube is removable from the core tube;
wherein the core tube comprises an outer core tube and the flanged end cushion further comprises an inner core tube removably coupled to the outer core tube within the outer core tube; and
wherein the annular ring surrounding the core tube comprises one or more annular rings each having an annular space therein, the one or more annular rings formed as one or more pessary rings positioned around the outer core tube between the lower lip of the cervical cup and the cushion lip of the flanged end cushion, each of the one or more pessary rings comprising a ring opening sized such that the lower lip of the cervical cup and the cushion lip of the flanged end cushion inhibit removal of the one or more pessary rings from the cervical support device, each of the one or more pessary rings detachably coupled to the outer core tube or the inner core tube, one of the one or more pessary rings abutting against, and being in contact with, the cushion lip of the flanged end cushion.

2. The cervical support device of claim 1, further comprising an anterior stiffening shoulder positioned between the lower lip of the cervical cup and the core tube, and wherein the flanged end cushion comprises a curved recess between the cushion lip and the opening of the end cushion.

3. The cervical support device of claim 1, wherein the inner core tube comprises a plurality of ribs engaged with a plurality of ribs on the outer core tube.

4. The cervical support device of claim 1, wherein the one or more pessary rings comprise at least two pessary rings having different outer diameters.

5. A cervical support device for long term placement entirely within a woman's vagina during pregnancy for the purpose of supporting the woman's uterus against early onset of labor, the cervical support device comprising:
a cervical cup configured to receive a cervix extending from a uterus through cervical fornices, the cervical cup comprising a void sized to surround an outer surface of the cervix and directly engage the cervical fornices but not the cervix when placed within a vagina, a vent, an upper lip proximate the void, a lower lip extending from a base of the cervical cup below the void;
a core tube assembly comprising a first core tube fixedly coupled to the cervical cup, a second core tube removably coupled to the first core tube, and a core tube passage extending through the first and second core tubes and in fluid communication with the vent of the cervical cup;
an annular ring having an annular space therein, the annular ring surrounding the core tube assembly and removably mounted thereon; and
a flanged end cushion coupled to the second core tube such that the annular ring is disposed between the flanged end cushion and the lower lip of the cervical cup and the flanged end cushion and the lower lip are in contact with the annular ring, the flanged end cushion comprising an opening in fluid communication with the core tube passage and a cushion lip surrounding the opening;
wherein the cervical device is configured for placement entirely within the vagina where positioning of the upper lip of the cup against the cervical fornices is maintained by the annular ring engaging a vaginal wall of the vagina.

6. The cervical support device of claim 5, wherein the first core tube comprises an outer core tube and the second core tube comprises an inner core tube integrally formed with the flanged end cushion and removably coupled to the outer core tube within the outer core tube.

7. The cervical support device of claim 6, wherein the inner core tube comprises a plurality of ribs engaged with a plurality of ribs on the outer core tube.

8. The cervical support device of claim 7, wherein the annular ring surrounding the core tube assembly comprises one or more annular rings in the form of one or more pessary rings positioned around the outer core tube and between the lower lip of the cervical cup and the cushion lip of the flanged end cushion, each of the one or more pessary rings comprising a ring opening sized such that the lower lip of the cervical cup and the cushion lip of the flanged end cushion inhibit removal of the one or more pessary rings from the cervical support device, one of the one or more pessary rings abutting against, and being in contact with, the cushion lip of the flanged end cushion.

9. The cervical support device of claim 8, wherein the one or more pessary rings comprise at least two pessary rings having different outer diameters.

10. The cervical support device of claim 5, wherein the annular ring further comprising an inflatable balloon surrounding the core tube assembly and positioned such that the inflatable balloon does not extend beyond the lower lip of the cervical cup when the inflatable balloon is in an inflated state.

11. The cervical support device of claim 10, wherein the first core tube comprises an upper core tube coupled to the base of the cervical cup and the second core tube comprises a lower core tube threadedly coupled to the upper core tube opposite the cervical cup, the end cushion being coupled to the lower tube opposite the upper tube, and wherein the lower core tube is adjustable between at least an extended position and a retracted position wherein the end cushion is closer to the cervical cup than when the lower core tube is in the extended position.

12. The cervical support device of claim 11, wherein the flanged end cushion comprises a curved recess facing the cervical cup and between the cushion lip and the opening of the flanged end cushion.

13. A cervical support device for placement entirely within a woman's vagina during pregnancy for an extended period of time for the purpose of supporting the woman's uterus and stabilizing the woman's cervix against early onset of labor, the cervical support device comprising:
 a cervical cup configured to receive a cervix extending from a uterus through cervical fornices, the cervical cup comprising a void sized to surround an outer surface of the cervix and directly engage the cervical fornices but not the cervix when placed within a vagina, a vent, an upper lip proximate the void, a lower lip extending from a base of the cervical cup;
 a core tube fixedly coupled to the cervical cup and comprising a core tube passage in fluid communication with the vent of the cervical cup;
 an annular ring comprising an annular hollow therein, the annular ring surrounding the core tube and removably mounted thereon; and
 a flanged end cushion detachably coupled to the core tube, the flanged end cushion comprising an opening in fluid communication with the core tube passage, a cushion lip surrounding the opening, and a curved recess between the cushion lip and the opening of the flanged end cushion, wherein the annular ring is seated in the curved recess and supports the lower lip of the cervical cup;
wherein the cervical device is configured for placement entirely within the vagina where positioning of the upper lip of the cup against the cervical fornices is maintained by the annular ring engaging a vaginal wall of the vagina.

14. The cervical support device of claim 13, further comprising:
 an inflation passage within a wall of the core tube, the inflation passage extending from an end opening on a terminating end of the core tube opposite the cervix cup to a wall opening on the wall of the core tube;
 an inflation valve positioned within the inflation passage and configured to inflate a balloon within the annular ring that is coupled to the core tube; and
 a sealing plug coupled to the end opening of the inflation passage and configured to plug the end opening.

15. The cervical support device of claim 14, wherein the inflatable balloon surrounds the core tube assembly and is positioned such that an inner chamber of the inflatable balloon is in fluid communication with the inflation passage and the inflatable balloon does not extend beyond the lower lip of the cervical cup when the inflatable balloon is inflated.

16. The cervical support device of claim 13, further comprising an anterior stiffening shoulder positioned between the lower lip of the cervical cup and the core tube.

\* \* \* \* \*